(12) United States Patent
Murphy et al.

(10) Patent No.: US 10,379,093 B2
(45) Date of Patent: *Aug. 13, 2019

(54) METHOD AND DEVICE FOR DETECTING ODORANTS IN HYDROCARBON GASES

(71) Applicant: Battelle Memorial Institute, Columbus, OH (US)

(72) Inventors: Michael J. Murphy, Dublin, OH (US); Michael J. Swickrath, Delaware, OH (US)

(73) Assignee: Battelle Memorial Institute, Columbus, OH (US)

( * ) Notice: Subject to any disclaimer, the term of this patent is extended or adjusted under 35 U.S.C. 154(b) by 387 days.

This patent is subject to a terminal disclaimer.

(21) Appl. No.: 15/101,215

(22) PCT Filed: Dec. 8, 2014

(86) PCT No.: PCT/US2014/069071
§ 371 (c)(1),
(2) Date: Jun. 2, 2016

(87) PCT Pub. No.: WO2015/085298
PCT Pub. Date: Jun. 11, 2015

(65) Prior Publication Data
US 2016/0305920 A1  Oct. 20, 2016

Related U.S. Application Data

(60) Provisional application No. 61/912,809, filed on Dec. 6, 2013.

(51) Int. Cl.
*G01N 33/00* (2006.01)
*G01N 29/02* (2006.01)
(Continued)

(52) U.S. Cl.
CPC ....... *G01N 33/0001* (2013.01); *G01N 29/022* (2013.01); *G01N 29/036* (2013.01);
(Continued)

(58) Field of Classification Search
CPC ............. G01N 33/0001; G01N 29/022; G01N 29/036; G01N 29/226; G01N 29/30;
(Continued)

(56) References Cited

U.S. PATENT DOCUMENTS 3,374,659 A   3/1968  Sanford et al.
3,677,066 A * 7/1972  King, Jr. .............. G01N 29/036
                                                73/246.06
(Continued)

FOREIGN PATENT DOCUMENTS

EP    0445927 A2   9/1991
WO    99/47905 A2  9/1999

OTHER PUBLICATIONS

Akerfeldt et al., "Spectrophotometric Determination of Disulfides, Sulfinic Acids, Thio Ethers, and Thiols with the Palladium (II) Ion", Analytical Biochemistry, 1964, vol. 8, pp. 223-228.
(Continued)

*Primary Examiner* — Marrit Eyassu
(74) *Attorney, Agent, or Firm* — MacMillan, Sobanski & Todd, LLC

(57) ABSTRACT

A dual quartz crystal microbalance (QCM) sensor is disclosed for use in a hand-held detection device (10) for detecting the presence of an odorant in hydrocarbon gaseous fuels. The odorant is a thiol-based compound, such as ethanethiol. One QCM (16) is coated with a coating typically containing a reagent that specifically reacts with the thiol of the odorant and alters its oscillation frequency as a result of mass gained in the reaction. A second QCM (16') serves as a control and the two frequency signals may be
(Continued)

heterodyned (26) to produce a delta-frequency representative of the mass change. Circuitry and signal processing (32) are used to produce a final result correlated to the level of thiol in the hydrocarbon gas.

20 Claims, 14 Drawing Sheets

(51) Int. Cl.
*G01N 29/036* (2006.01)
*G01N 29/22* (2006.01)
*G01N 29/30* (2006.01)

(52) U.S. Cl.
CPC ............ *G01N 29/226* (2013.01); *G01N 29/30* (2013.01); *G01N 33/0044* (2013.01); *G01N 2291/021* (2013.01); *G01N 2291/0255* (2013.01); *G01N 2291/0256* (2013.01); *G01N 2291/0426* (2013.01)

(58) Field of Classification Search
CPC ......... G01N 33/0044; G01N 2291/021; G01N 2291/0255; G01N 2291/0256; G01N 2291/0426
USPC .................................................. 73/23.34
See application file for complete search history.

(56) References Cited

U.S. PATENT DOCUMENTS

| | | | |
|---|---|---|---|
| 3,863,495 A | 2/1975 | Schulz et al. | |
| 3,960,494 A | 6/1976 | Verma et al. | |
| 5,506,059 A * | 4/1996 | Robbins ............. | A61B 5/04087 428/457 |
| 5,996,396 A | 12/1999 | Marshall et al. | |
| 6,196,052 B1 * | 3/2001 | May ........................ | B01D 53/30 73/24.06 |
| 6,773,926 B1 * | 8/2004 | Freund ................... | G01N 31/22 436/111 |
| 6,839,636 B1 | 1/2005 | Sunshine et al. | |
| 6,883,364 B2 | 4/2005 | Sunshine et al. | |
| 6,888,629 B1 | 5/2005 | Boss et al. | |
| 7,966,132 B2 | 6/2011 | Lewis et al. | |
| 9,032,782 B1 * | 5/2015 | Van Deusen .......... | G01N 33/50 204/403.02 |
| 2002/0023480 A1 * | 2/2002 | Hattori ................... | G01N 27/12 73/31.05 |
| 2002/0124631 A1 | 9/2002 | Sunshine et al. | |
| 2002/0142477 A1 * | 10/2002 | Lewis ................. | G01N 33/0031 436/151 |
| 2005/0061056 A1 | 3/2005 | Sunshine et al. | |
| 2006/0161320 A1 | 7/2006 | Cahoon | |
| 2008/0297044 A1 | 12/2008 | Jun et al. | |
| 2009/0142112 A1 | 6/2009 | Gervasi et al. | |
| 2009/0289213 A1 | 11/2009 | Pipper et al. | |
| 2010/0231899 A1 * | 9/2010 | Hulko ..................... | C12Q 1/005 356/218 |
| 2011/0236992 A1 | 9/2011 | Lee et al. | |
| 2012/0100636 A1 * | 4/2012 | Johal ................ | G01N 33/54373 436/501 |
| 2012/0129270 A1 | 5/2012 | Nallani et al. | |
| 2012/0301827 A1 | 11/2012 | Hatanaka et al. | |
| 2012/0330274 A1 | 12/2012 | Hyde et al. | |
| 2013/0042672 A1 * | 2/2013 | Kukita ................. | G01N 29/036 73/61.49 |
| 2015/0111765 A1 * | 4/2015 | Laury-Kleintop ... | G01N 29/022 506/9 |
| 2016/0231267 A1 * | 8/2016 | Swager ................ | G01N 27/127 |

OTHER PUBLICATIONS

Borgstrom et al., "Quantitative Determination of Mercaptans in Naphtha", Industrial and Engineering Chemistry, 1929, vol. 1, No. 4, pp. 186-187.
Cecil, "The Quantitative Reactions of Thiols and Disulphides with Silver Nitrate," Thiols and Disulphides with Silver Nitrate, 1950, vol. 47, pp. 572-584.
Cecil et al., "The Estimation of Thiols and Disulphides by Potentiometric Titration with Silver Nitrate", Estimation of Thiols and Disulphides, 1955, vol. 59, pp. 234-240.
Dunham et al., "Dual Quartz Crystal Microbalance", Analytical Chemistry, 1995, vol. 67, pp. 267-272.
Ellis et al., "Determination of Thiols in Hydrocarbon Gases", Analytical Chemistry, 1951, vol. 23, No. 21, pp. 1777-1779.
ESI, "Propane Odorant Confirmation, Independent Examiner's Report", Massachusetts Office of Attorney General, State Fire Marshal, ESI File No. 33057T, 2010, pp. 1-23.
Hankinson et al., "Vapor-Liquid Equilibrium Data for Ethyl Mercaptan in Propane Vapors", Gas Processors Association, Proceedings of Fifty-Third Annual Convention, pp. 98-100.
Hlavay et al., "Applications of the Piezoelectric Crystal Detector in Analytical Chemistry", Analytical Chemistry, 1977, vol. 49, No. 13, pp. 1890-1898.
Hongmei et al., "An Application of Artificial Neural Networks. Simultaneous Determination of the Concentration of Sulfur Dioxide and Relative Humidity with a Single Coated Piezoelectric Crystal", Analytical Chemistry, 1997, vol. 69, pp. 699-702.
Horowitz, "Chapter 5: Active Filters and Oscillators; 5.19 Quartz-crystal oscillators", The Art of Electronics, 1989, pp. 300-302.
Hussien et al., "Study the Sensitivity of Quartz Crystal Microbalance (QCM) Sensor Coated with Different Thickness of Polyaniline for Determination Vapours of Ethanol, Propanol, Hexane and Benzene", Chemistry and Materials Research, 2013, vol. 3, No. 5, pp. 61-65.
Joo et al., "ZnO nanorod-coated quartz crystals as self-cleaning thiol sensors for natural gas fuel cells", Sensors and Actuators B: Chemical, 2009, vol. 138, pp. 485-490.
Kikuchi et al., "Quartz crystal microbalance (QCM) sensor of CH3SH gas by using polyelectrolyte-coated sol-gel film", Sensors and Actuators B, 2005, vol. 108, pp. 564-571.
Knight et al., "Measurement of Odorant Levels in Natural Gas", Industrial & Engineering Chemistry Product Research and Development, 1976, vol. 15, No. 1, pp. 59-63.
Lichter, "Crystals and Oscillators", JL9113 Rev. B, pp. 1-16.
Maji et al., "Polymer-Coated Piezoelectric Quartz Crystal Sensor for Sensing the Nerve Agent Simulant Dimethyl Methylphosphonate Vapor", Journal of Applied Polymer Science, 2010, vol. 116, Issue 6, pp. 3708-3717, Abstract Only.
McConnaughey, "Rapid detection method for mercaptans", Gas, 1971, vol. 47, No. 8, pp. 54-55, Abstract Only.
Schindler et al., "Determination of Mercaptan Sulfur Content of Gasolines and Naphthas: Effect of Mercuric Sulfide and Elementary Sulfur", Industrial and Engineering Chemistry, 1941, vol. 13, No. 5, pp. 326-328.
Si et al., "Polymer coated quartz crystal microbalance sensors for detection of volatile organic compounds in gas mixtures", Analytica Chimica Acta, 2007, vol. 597, pp. 223-230.
Texas Instruments, "LM2907/LM2917 Frequency to Voltage Converter", SNAS555C, Jun. 2000, pp. 1-32.
Texas Instruments, "Wide Bandwidth Precision Analog Multiplier", SBFS017A, Dec. 1995, pp. 1-8 and addendum.
Vashist et al., "Recent Advances in Quartz Crystal Microbalance-Based Sensors", Journal of Sensors, 2011, Article ID 571405, pp. 1-14.
PCT International Search Report and Written Opinion, Application No. PCT/US2014/069071, dated Mar. 12, 2015.

* cited by examiner

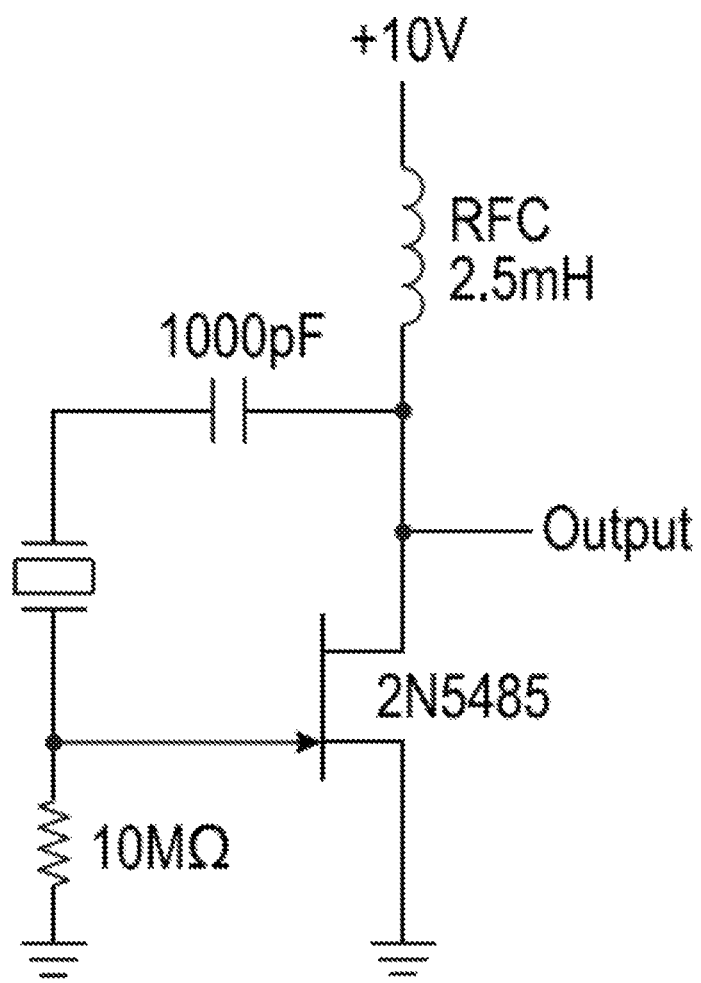
Prior Art – Fig. 3 (subpart A)

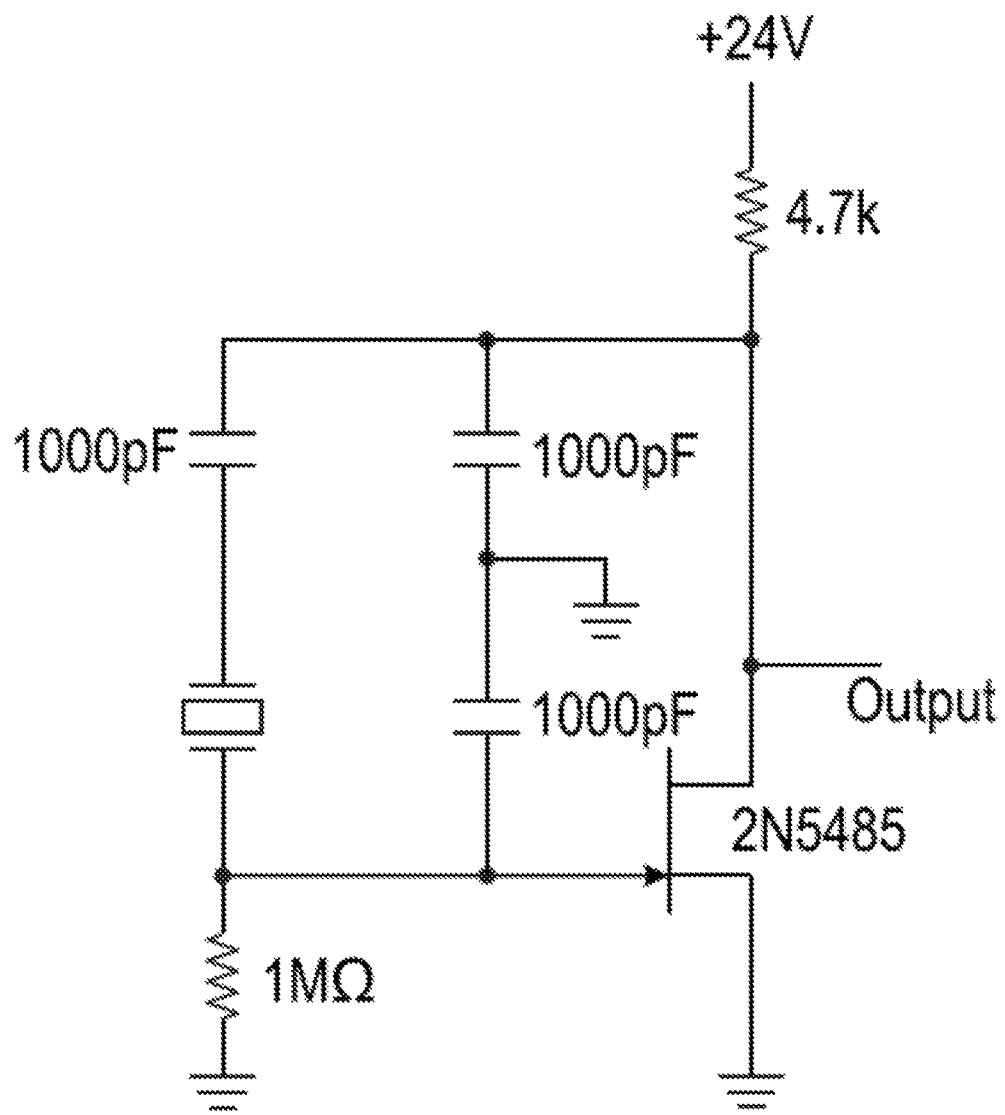
Prior Art – Fig. 3 (subpart B)

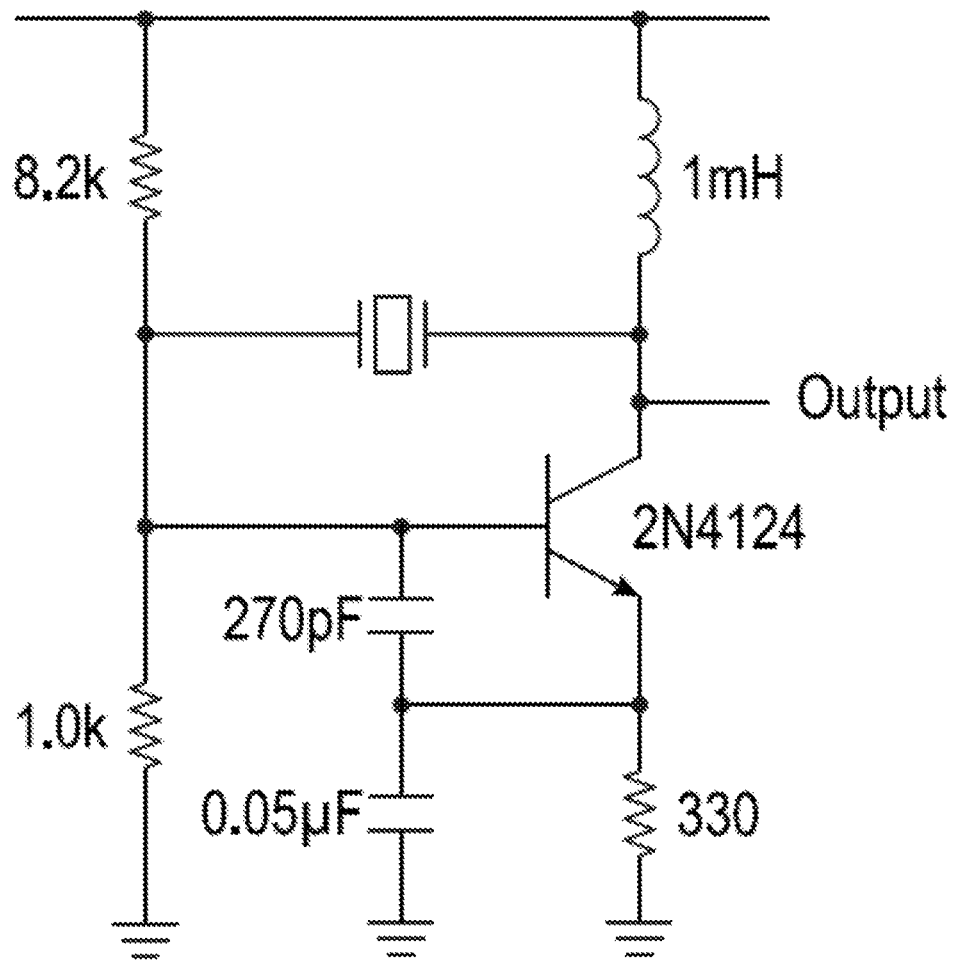
Prior Art – Fig. 3 (subpart C)

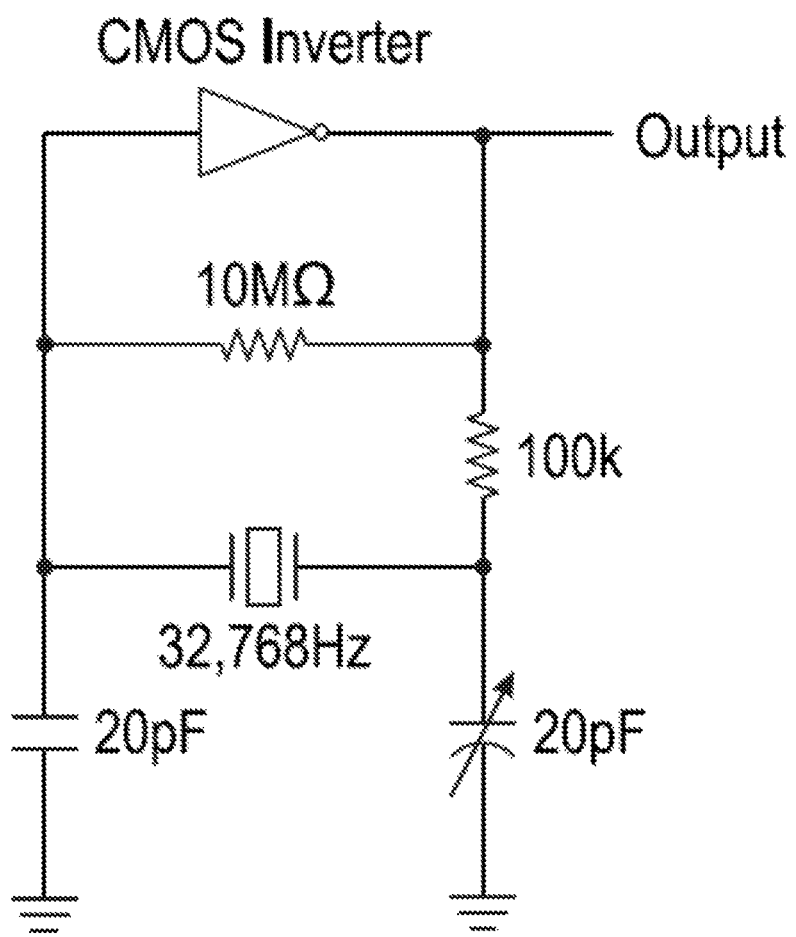
Prior Art – Fig. 3 (subpart D)

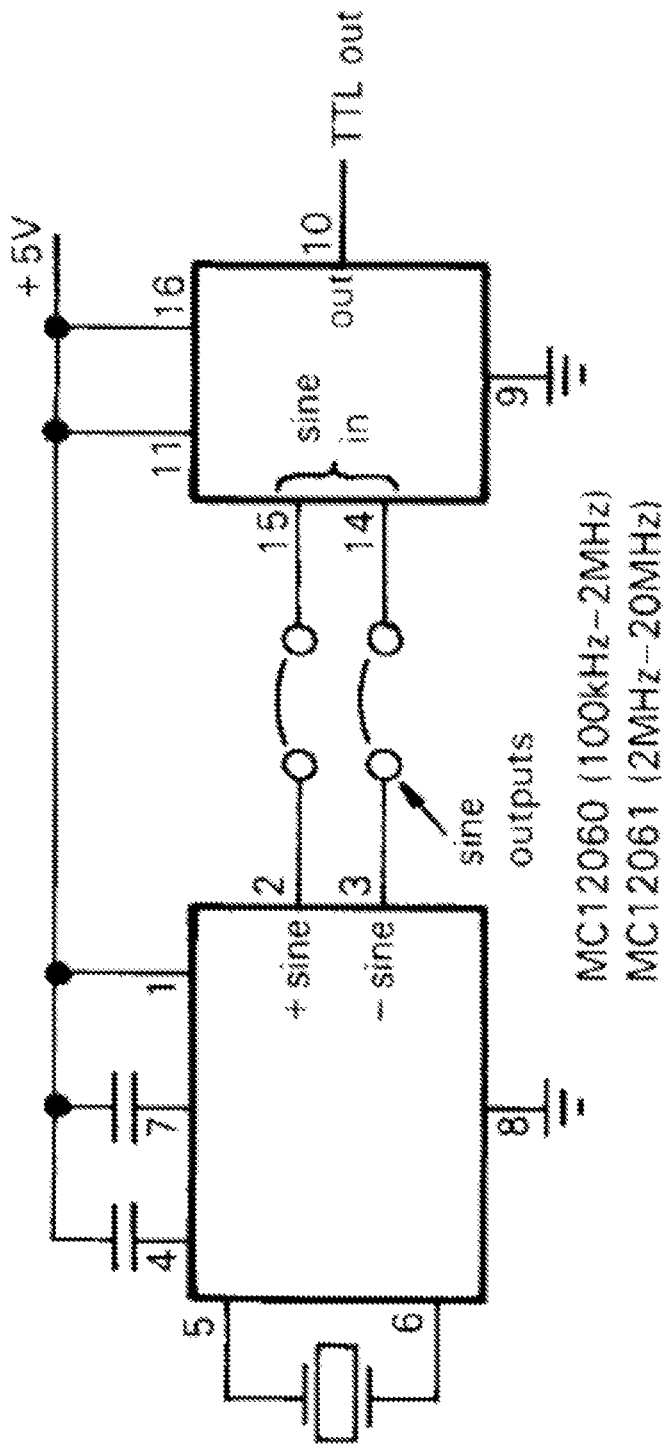
Prior Art – Fig. 3 (subpart E)

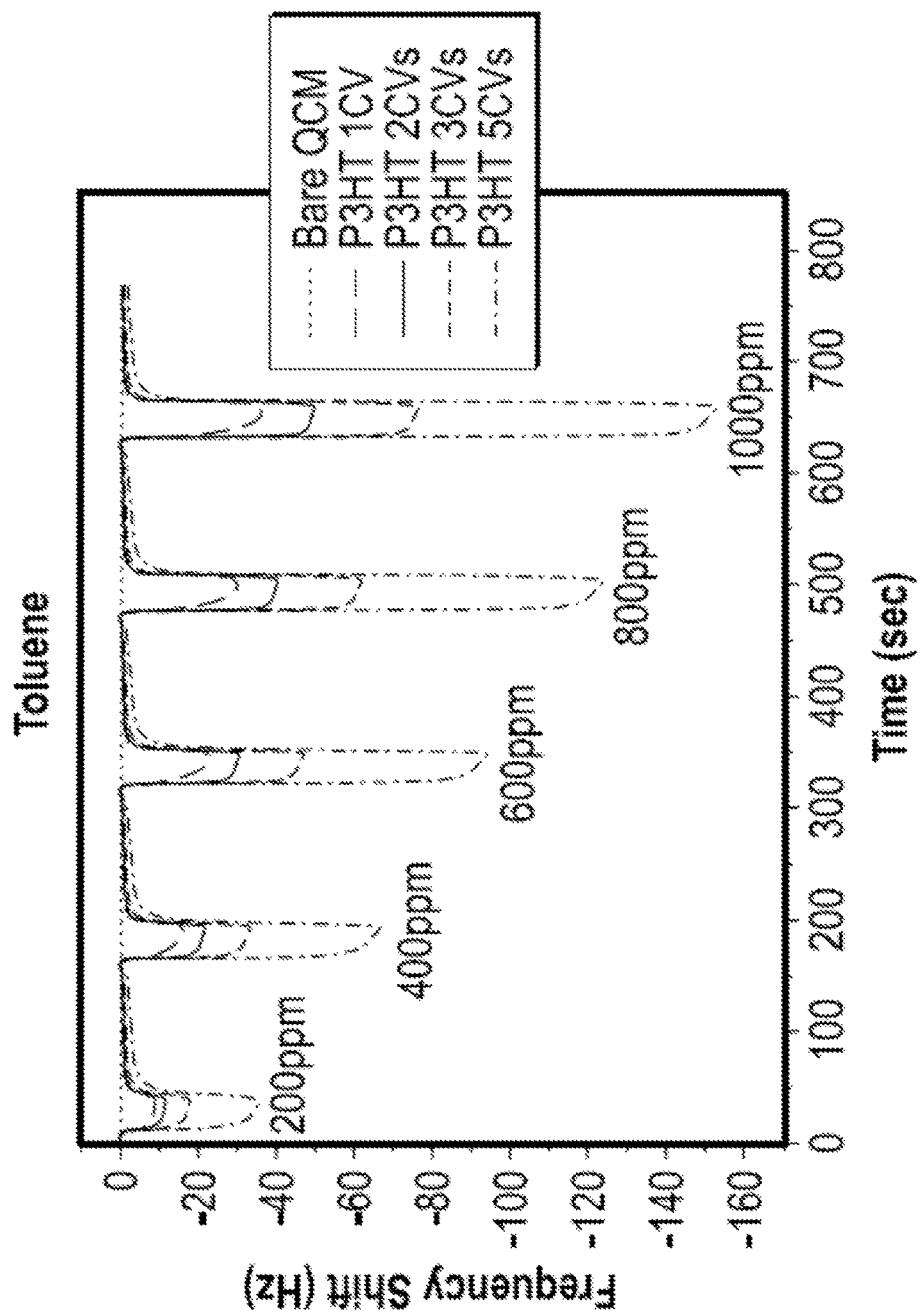
Prior Art – Fig. 4 (subpart A)

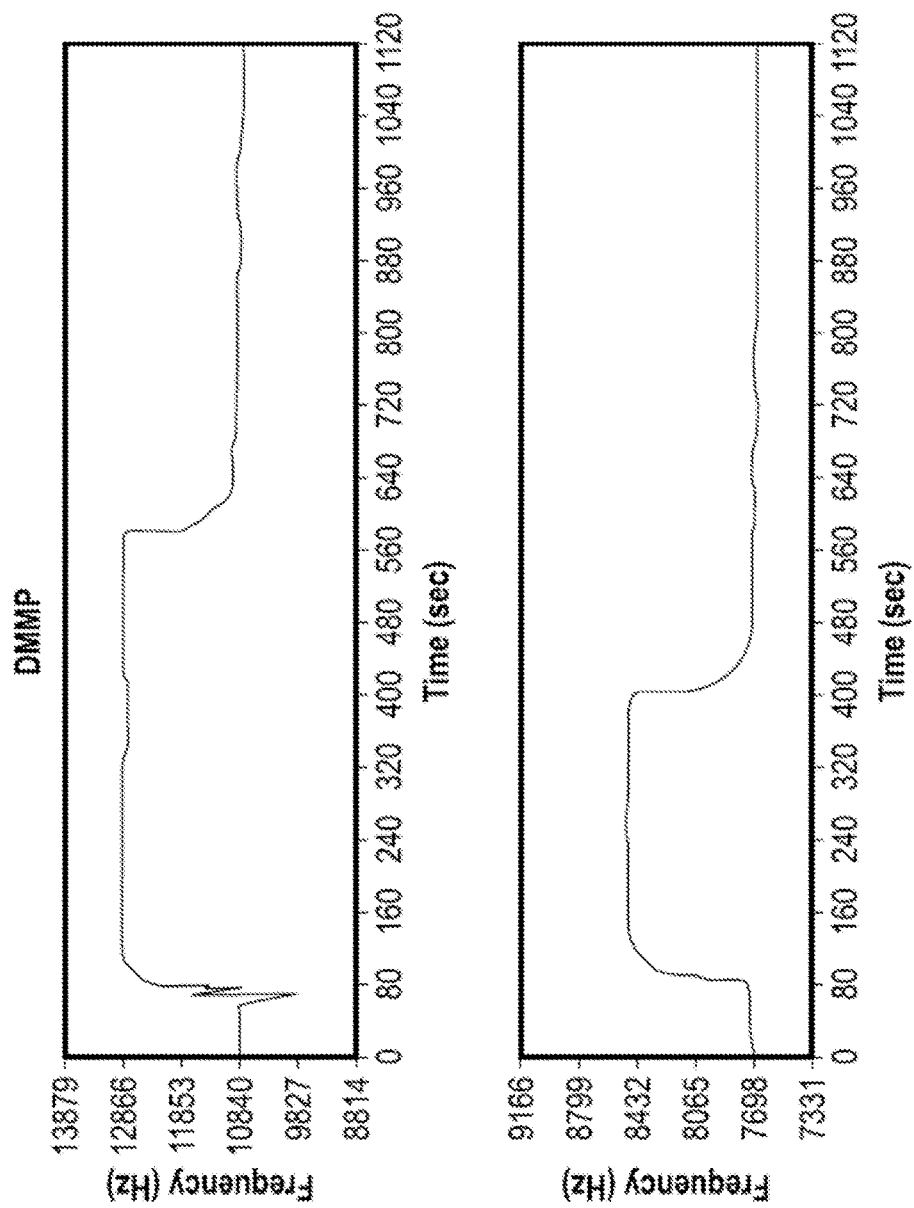
Prior Art – Fig. 4 (subpart B)

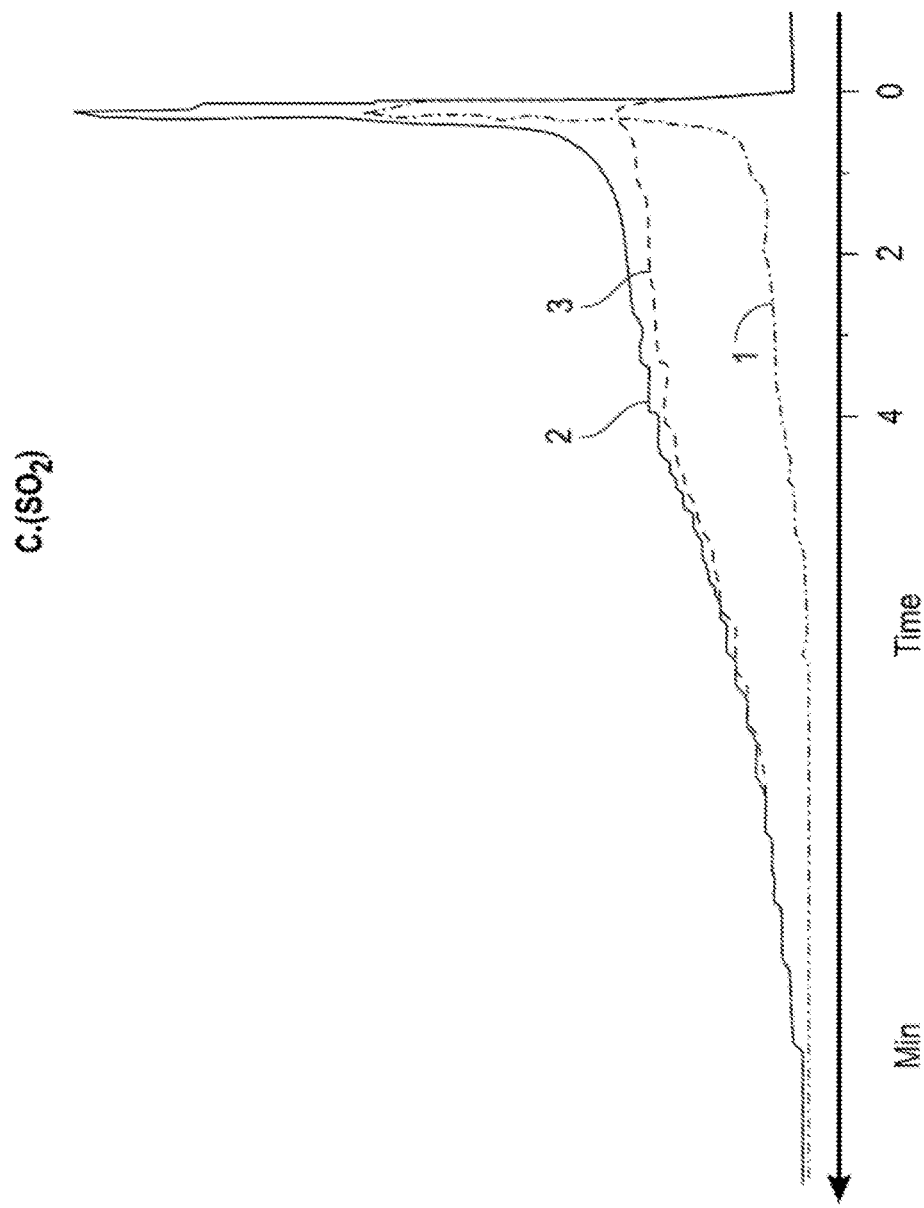
Prior Art – Fig. 4 (subpart C)

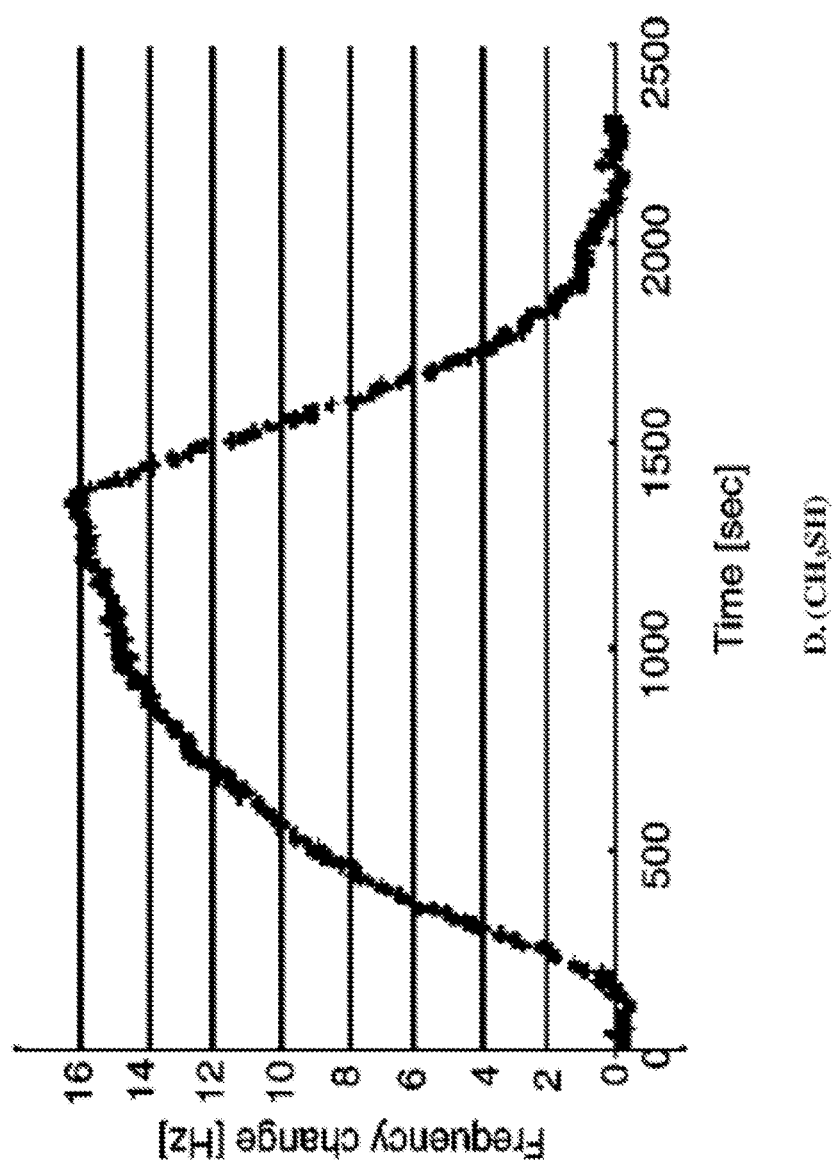
Prior Art – Fig. 4 (subpart D)

METHOD AND DEVICE FOR DETECTING ODORANTS IN HYDROCARBON GASES

This is a national stage application filed under 35 USC § 371 of international application PCT/US2014/069071 filed Dec. 8, 2014 which claims priority from provisional application Ser. No. 61/912,809 filed Dec. 6, 2013.

TECHNICAL FIELD

The present invention relates to the field of detecting odorants added to hydrocarbon gases and, more specifically, to a quartz crystal microbalance (QCM) device and method of using it for detecting thiol-containing odorants added to hydrocarbon gases such as propane, LPG or natural gas.

BACKGROUND OF THE INVENTION

Potentially explosive hydrocarbon fuel gases such as propane have been odorized to warn of leaks. Although the use of odorants to warn of leaks of gaseous fuels was first proposed in Germany by Von Quaglios in the 1800s, and odorants were used as early as 1900 in Europe; it was not until 1937 when a school explosion in Texas provided sufficient impetus for promulgation of U.S. laws requiring the addition of an odorant to gaseous fuels. Currently, both natural gas and propane are required to be odorized such that most people can detect the odor at ⅕ the lower flammability limit. For example, 29 CFR 1910.119 (b)(1)(i) states that "liquefied petroleum gases shall be effectively odorized by an approved agent of such character as to indicate positively, by distinct odor, the presence of gas down to concentration in air of not over one-fifth the lower limit of flammability . . . the odorization requirement of paragraph (b)(1)(i) of this section shall be considered to be met by the use of 1.0 pounds of ethyl mercaptan per 10,000 gallons of LP-gas." The requirements under 49 CFR 173.315 (b) (1) are the same.

Ethyl mercaptan, also known as ethanethiol, is the odorant of choice for 95 percent of the propane industry. However, it must be noted that although tests have shown about 9 out of 10 people can smell ethanethiol at a level of 20 ppb, this still leaves a significant number of people for whom smell is not a reliable indicator of odorant level.

An additional problem known as "odorant fade" was well documented by Beltis in "*Characterization of LP Gas Odor and Fade*," Kevin J. Beltis, Consumer Products Safety Commission report CPSC-C-86-1281, June 1986, and it may also reduce the ability to detect leaks. Odorant fade is the loss of odorant effectiveness caused by absorption, adsorption, complexation and/or degradation of the odorant. For example, most odorants can be absorbed by materials with a high surface area, such as soil or dirt. Absorption/adsorption may also occur on the surfaces of new pipes or tanks that have not previously contained odorized propane. Moreover, odorants may be chemically oxidized or otherwise chemically transformed to products (e.g. disulfides) that do not have the same degree of odor warning capability. In particular, rust in tanks is known to cause thiols (mercaptans), such as ethanethiol to oxidize to compounds of lower odor. Collectively, these absorption, adsorption, complexation and degradation phenomena are known as odor fade. Due to odor fade, there remain cases where there is doubt about the amount of odorant present in commercial propane. A recent example is the controversy about odorization levels in LP gas supplied to customers in Massachusetts and Connecticut that was reported in the March 2011 issue LP Gas Magazine.

Leakages of inadequately odorized gas present a high risk of inadvertent ignition and explosion since the ability to detect such leaks is diminished. Thus, there is a need to verify that propane fuel in fact contains the proper level of odorant. The three most common methods of testing for propane odorant are a) the "sniff" test, b) stain tubes, and c) gas chromatography. Optical methods are sometimes used in a laboratory setting. Note that odor fade can occur after delivery. Even if the propane was delivered to the supplier's tank with the proper odorant level or the propane was delivered to the customer's tank with the proper odorant level there is no certainty that the propane supplied to the customer's point of use has the proper odorant level. Testing may be needed along the entire supply chain from production to point of use.

The most basic type of test for odorant is simply a sniff test. However, it is well-known that such a test result may be subjective. There are devices that make the test semi-quantitative by diluting the sample with known quantities of air. Examples include the Heath Odorator, and the Bacharach Odorometer, developed in the 1920s. The Odorometer had drawbacks however: it required ambient air for dilution of the odor and the air had to be passed through multiple filters to remove impurities that otherwise could affect the perceived odor intensity.

Stain tubes, or length-of-stain tubes, have been used for the determination of odorant concentration. For example, Sensidyne and Draeger manufacture hermetically sealed thin glass tubes that contain a detecting reagent that produces a distinct color change when a sample of odorized propane vapor is drawn through the tube. If ethyl mercaptan is present, the detecting reagent produces a colored stain that can be measured with a calibration scale that is printed on the tube. Additionally, there is an ASTM standard for such stain tubes (Standard Test Method for Determination of Ethyl Mercaptan in Natural Gas, ASTM D5305, 2007).

Although length-of-stain tubes have a long history and enjoy ASTM Standard recognition, they have not proved fully satisfactory in the field, as the reading is somewhat subjective and the underlying accuracy is insufficient. According to ASTM Standards D1988 and D5305, the accuracy (reproducibility) of length-of-stain tubes for mercaptan measurement in gaseous fuels is plus or minus 20 to 25 percent or more. A previous Bureau of Mines study came to a similar conclusion. Moreover, visual assessment of color change is inherently subjective; some people are unable to distinguish certain colors.

At the more complex end of the analytical scale, gas chromatography can be very accurate in the laboratory, but is too expensive and awkward (bulky equipment and a compressed carrier gas supply are required) for use in the field. Similarly, Fourier transform infrared spectroscopy (FTIR), nondispersive infrared spectroscopy (NDIR), and laser-based optical absorption techniques can be sensitive, accurate, and free from interferences, but they are also complex and expensive procedures.

At least one vendor (Leister Technologies AG, Galileo-Strasse 10 CH-6056 Kaegiswil/Switzerland—See more at: http://www.leister.com/en/) offers a commercial laser diode spectrometer that could be suitable for mercaptan measurement. But this gas detector costs thousands of dollars exclusive of the power supply, sample pump, and sampling handling components.

The need for an inexpensive and portable detector that can monitor odorant concentrations along the entire supply line greatly complicates the development of an odorant meter. It means that an odorant meter cannot be a complex or expensive device that is used only at a production plant or at a supplier's headquarters. The meter must be portable and practical for field use by delivery and service personnel who are normally at the customer's premises.

These and other problems are addressed by the present invention.

SUMMARY OF THE INVENTION

In a first aspect, the invention includes a portable device for detecting thiol odorants in a hydrocarbon gas, the device comprising in a housing:
  a power source for producing a current;
  a thiol sensor comprising
  a piezo-crystalline substrate disposed in the housing and located for fluid communication with the hydrocarbon gas,
  a coating on the piezo-crystalline substrate, the coating capable of reacting specifically with and capturing thiol components from a gaseous phase, while substantially not reacting with the hydrocarbon gas itself;
  an oscillator circuit, the thiol sensor forming a part of the oscillator circuit, whereby, upon receiving a current input from the power source, the piezo-crystalline substrate oscillates at a first frequency prior being exposed to thiol odorants in a gas, and at a second frequency after being exposed to thiol odorants in the gas and capturing thiols in the coating, the second frequency differing from the first frequency in proportion to the amount of thiol captured.

This single sensor embodiment relies on the temporal shift in frequency from a first time ($t_0$) to to a second time ($t_n$) where n is the elapsed time for exposure of the sensor to the hydrocarbon gas thought to contain thiol odorants. As more time elapses, more thiol becomes bound to the sensor and the added mass alters the oscillation frequency in a manner that correlates to the amount of thiol present.

In a second, dual sensor embodiment, the device comprises in a housing:
  a power source for producing a current,
  a reference sensor comprising a first piezo-crystalline substrate disposed in the housing and located for fluid communication with the hydrocarbon gas; the reference sensor forming part of a first oscillator circuit capable of producing a reference oscillation frequency in response to a current input;
  a thiol sensor comprising a second piezo-crystalline substrate disposed in the housing and located for fluid communication with the hydrocarbon gas; the second piezo-crystalline substrate having a coating thereon, the coating capable of reacting specifically with and capturing thiol components from a gaseous phase thereby adding mass to the thiol sensor, while substantially not reacting with the hydrocarbon gas itself; the thiol sensor forming part of a second oscillator circuit capable of producing a second oscillation frequency in response to a current input; and
  circuitry for heterodyning the first and second frequencies to produce a third frequency representative of the amount of mass added to the thiol sensor as a result of thiol capture.

The features in this paragraph may apply to either embodiment. The piezo-crystalline substrate may be a quartz crystal having a resonant frequency from about 1 to about 40 MHz, for example from about 2 MHz to about 20 MHz. The coating may comprise a reagent in a vehicle, for example, a reagent dispersed in an oleophobic solvent or vehicle. The vehicle may be a single solvent or a co-solvent system. The reagent may be a metal salt, and may include a metal from groups 10 or 11 of the periodic table, or a transition metal from period 5. The anion for salt formation may be any that is soluble or dispersible in the vehicle. For example, the following metal salts have proven useful: silver salts, such as silver nitrate or silver acetate; palladium salts, such as palladium nitrate or palladium chloride; and ruthenium nitrate.

In the dual sensor embodiment, the second sensor is typically a reference sensor and is used as to control for environmental variables like humidity and temperature that might become a source of erroneous response or unwanted "noise" in the frequency analysis. The reference sensor may be uncoated or coated. If coated, it may be coated with a vehicle similar to that used for the thiol sensor, but absent the thiol-specific reagent. Alternatively, an inert salt may take the place of the reagent salt to maintain comparable mass on the two sensors. In the dual sensor embodiment, a parallel oscillator circuit is employed, such as a Pierce or Colpitts circuit, to oscillate both crystals at their resonant frequency. The device may also include an analog multiplier circuit for heterodyning the first and second frequencies, and optionally, a frequency to voltage converter.

Various signal processing methods may be applied to the data to help refine the result and remove unwanted noise. For example, techniques are available for taking derivatives of curves or integrals representing the area under a curve; or for calculating moving averages and the like. Such signal processing may be performed on the analog data or on digital data through mathematical manipulations.

In another aspect the invention provides a method for detecting thiol odorants in a hydrocarbon gas using one of the devices described above. The hydrocarbon gas may be propane or natural gas, for example, and the odorant is typically ethanethiol, or methanethiol.

In its broadest aspect, the invention provides devices and methods for detecting a specific component of a gas mixture, comprising in a housing:
  a power source for producing a current,
  a reference sensor comprising a first piezo-crystalline substrate disposed in the housing and located for fluid communication with the gas mixture; the reference sensor forming part of a first oscillator circuit capable of producing a reference oscillation frequency in response to a current input;
  a test sensor comprising a second piezo-crystalline substrate disposed in the housing and located for fluid communication with the gas mixture; the second piezo-crystalline substrate having a coating thereon, the coating capable of reacting specifically with and capturing the specific component from the gas mixture, thereby adding mass to the test sensor, while substantially not reacting with other components of the gas mixture; the test sensor forming part of a second oscillator circuit capable of producing a second oscillation frequency in response to a current input; and
  circuitry for heterodyning the first and second frequencies to produce a third frequency representative of the amount of mass added to the test sensor as a result of capture of the specific component.

In this broadest sense of the invention, the specific component of interest in the gaseous mixture may react reversibly or irreversibly with the coating on the test sensor. The coating may contain a reagent that reacts with and binds the specific component of interest. The reference sensor may be coated or uncoated. If coated, the reference sensor may contain a coating of nearly identical mass to the coating on the test sensor. The reference coating may comprise the same coating as the test sensor minus the reagent. The reference coating may comprise the same coating as the test sensor substituting an inert salt for the reagent in an amount to match the mass of the reagent. The device is used in methods for detecting the specific component of interest as described herein for detecting thiols in hydrocarbon gas. Methods may include heterodyning two frequencies to produce a third, analog multipliers, frequency to voltage conversions, signal processing and the like.

Various other advantages of this invention will become apparent to those skilled in the art from the following detailed description of the preferred embodiment, when read in light of the accompanying drawings.

Prior art FIG. 3, in parts A through E, depict electronic circuit schematics for several types of known oscillator circuits useful with the invention.

Prior art FIG. 4, in parts A-D depict typical frequency response curves for QCM detectors of some known compounds.

Figure 5:
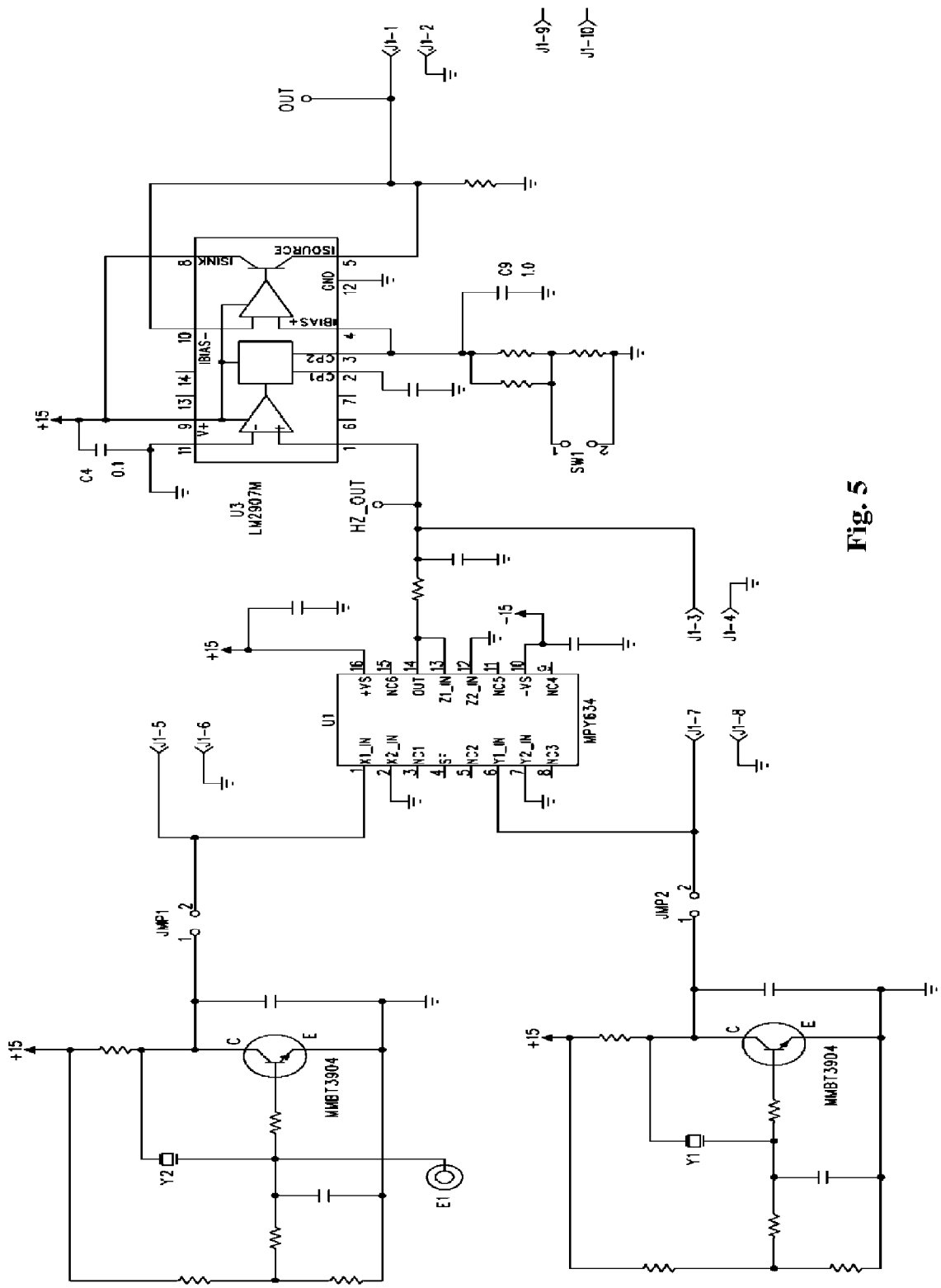

FIG. 5 is an electrical diagram of a specific parallel oscillator circuit.

Figure 6:
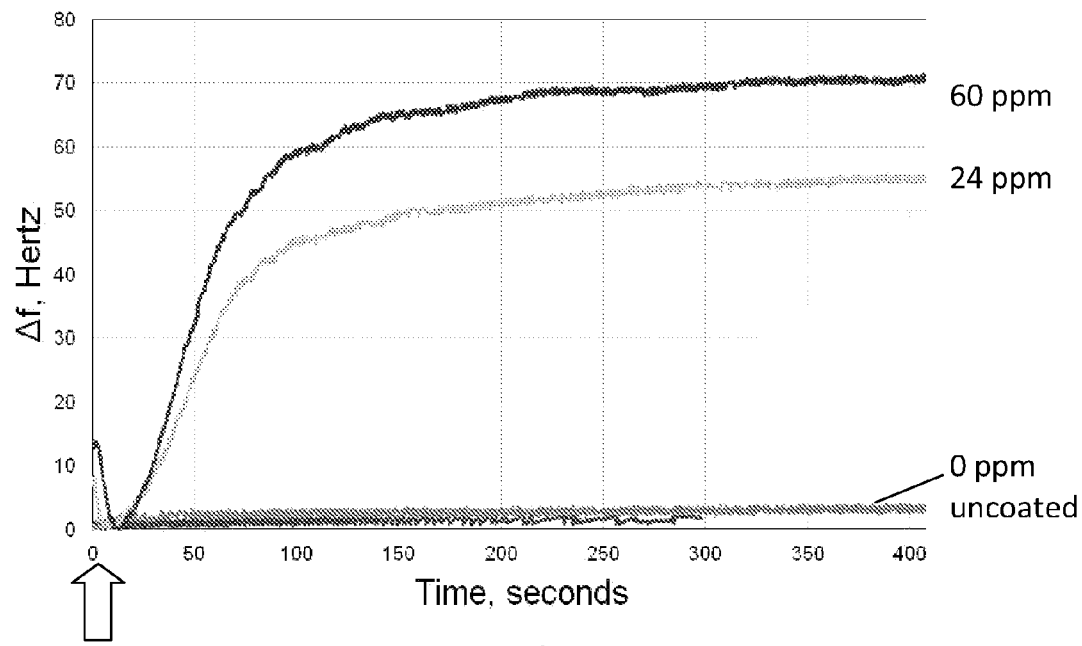

FIG. 6 is a chart illustrating the observed delta-frequency response for the system described in Example 2.

Figure 7:
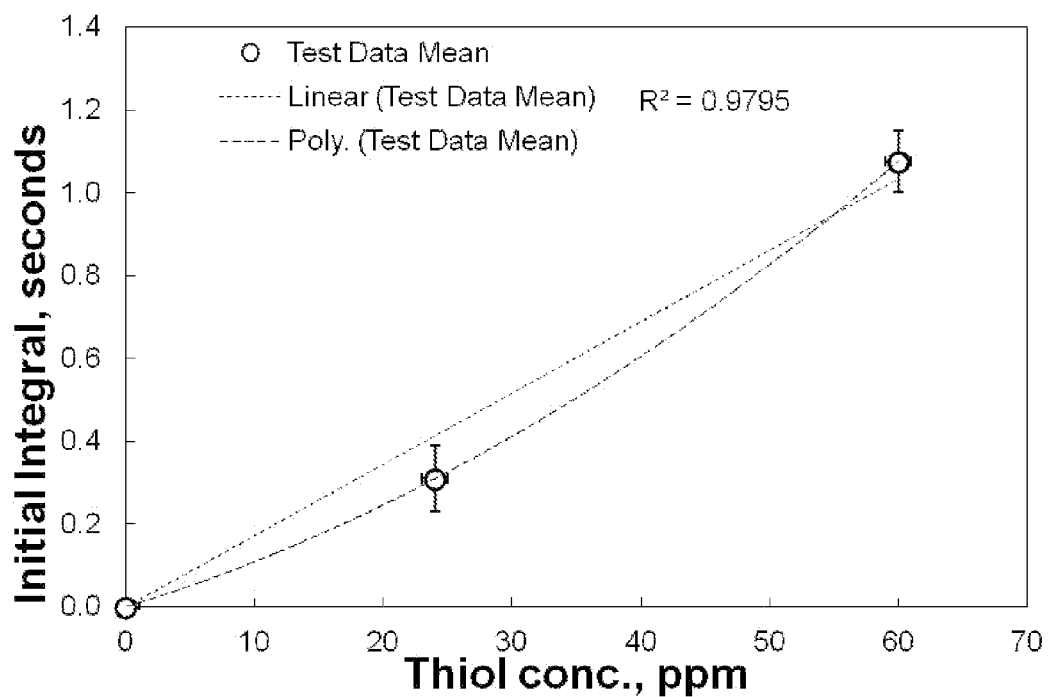

FIG. 7 depicts a calibration curve generated through various tests using signal processing techniques as described in Example 2.

Figure 8:
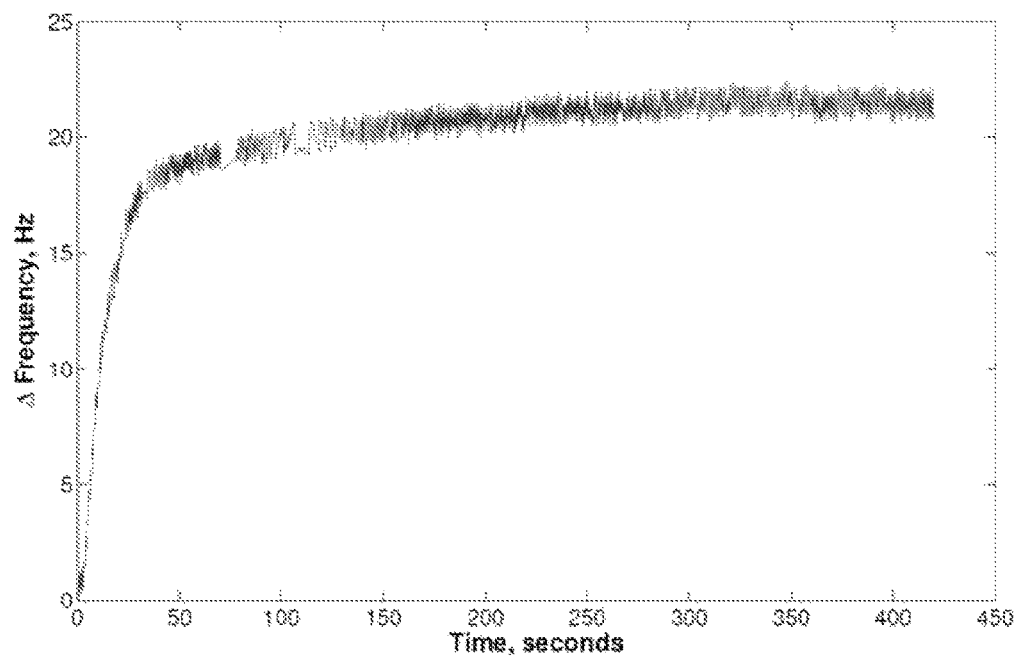
Figure 9:
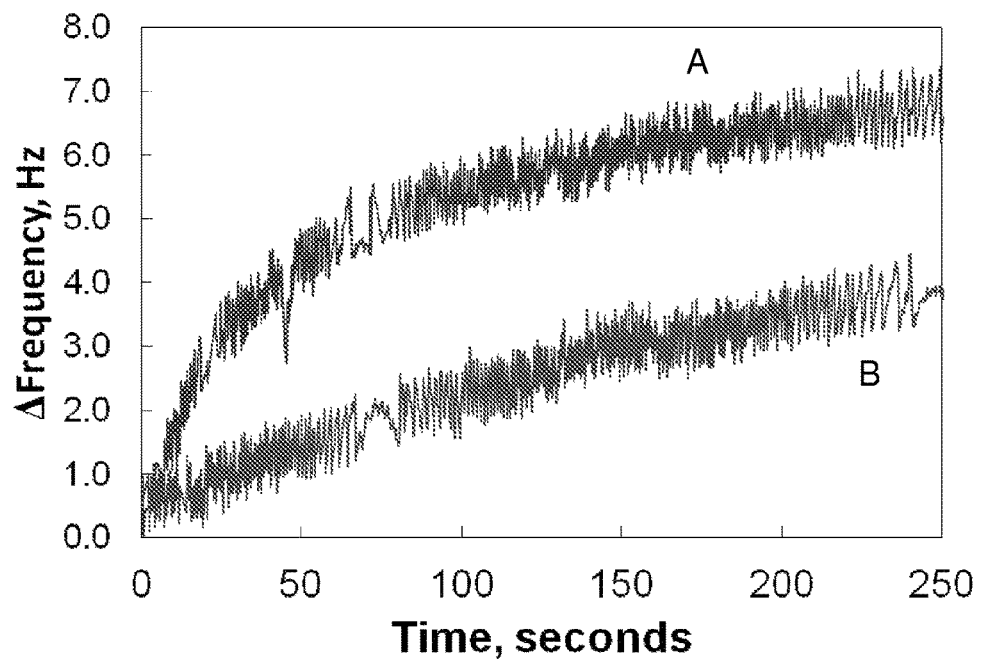

FIGS. 8 and 9 are graphs illustrating the delta frequency signal response for systems described in Examples 3, 4, and 6.

DETAILED DESCRIPTION OF THE INVENTION

Unless defined otherwise, all technical and scientific terms used herein have the same meaning as commonly understood by one of ordinary skill in the art to which the invention belongs. All references cited herein, including books, journal articles, published U.S. or foreign patent applications, issued U.S. or foreign patents, and any other references, are each incorporated by reference in their entireties, including all data, tables, figures, and text presented in the cited references.

In the drawings, the thickness of the lines, layers, and regions may be exaggerated for clarity.

Unless otherwise indicated, all numbers expressing ranges of magnitudes, such as angular degrees, percentages, quantities of ingredients, properties such as molecular weight, reaction conditions, and so forth as used in the specification and claims are to be understood as being modified in all instances by the term "about." This is due, in large part, to the fact that numerical values inherently contain certain errors necessarily resulting from their respective measurement systems. Accordingly, unless otherwise indicated, the numerical properties set forth in the specification and claims are approximations that may vary depending on the desired properties sought to be obtained in embodiments of the present invention. All numerical ranges are understood to include all possible integral sub-ranges within the outer boundaries of the range. Thus, a range of 30 to 90 percent discloses, for example, 35 to 51 percent, 45 to 85 percent, and 43 to 80 percent, etc.

Thiol Odorants in Hydrocarbon Gases

Hydrocarbon gases, as used herein, refer to compositions consisting mainly of straight or branched hydrocarbons having from 1 to 6 carbons. They are generally gaseous at room temperature and atmospheric pressure, but under sufficiently high pressures or sufficiently low temperatures they may become liquids. Because they are frequently distilled and condensed from various sources (e.g. petroleum, coal, etc) they frequently may not be completely pure, and may be a mixture or blend of various length hydrocarbons. Examples of hydrocarbon gases include methane, ethane, propane, butane and pentane, and mixtures thereof. Hydrocarbons longer than 4 carbons may be straight or branched. Also included within "hydrocarbon gases" are natural gas (a mixture that is predominantly methane), other blends of lower hydrocarbons, and compressed or liquid forms of these, such as LPG and CNG.

Thiol odorants have the general formula R—SH, where R is a hydrocarbon chain having from 1 to 6 carbons. Odorants include, for example, methanethiol, ethanethiol, propanethiol, butanethiol, and tetrahydrothiophene. The —SH, or thiol, group is known to impart the smell characterized often as "rotting eggs." Compounds containing it are variously referred to generally as thiols or mercaptans.

For commercial propane, the requirement for an odorant is deemed to be met by the addition of 1.0 pounds of ethanethiol, also known as ethyl mercaptan, to each 10,000 gallons of liquid propane. However, it is the general custom in the industry to add 1.5 pounds of ethanethiol to each 10,000 gallons.

Ethanethiol has the chemical formula $CH_3CH_2SH$. The boiling point of ethanethiol at atmospheric pressure is 35° C. Ethanethiol is moderately soluble in water with a solubility of 6.8 grams per liter.

In general and depending on the conditions, a compound partitions between a liquid phase and an adjacent vapor phase according to its partition coefficient, K. The equilibrium concentration of ethanethiol in the gas phase is thus different than that in the liquid phase, and this difference defines the so-called K ratio. Hankinson and Wilson report measured K ratio values for ethanethiol in propane ranging from 0.30 at 40° F. to 0.37 at 100° F. (See *Vapor-Liquid Equilibrium Data for Ethyl Mercaptan in Propane Vapors*, R. W. Handkinson, Grant M. Wilson, Proceedings of the Fifty-Third Annual Convention, 1974, page 98.) Thus, the 1.5 lb per 10,000 gallons treat rate amounts to about 36 ppm ethanethiol by mass in the liquid propane and, using a K ratio of 0.35, about 9 ppm ethanethiol by volume in the vapor. As used herein, "ppm" means parts per million, which may be expressed as on the basis of moles, mass or volume.

Thus, the level of ethanethiol odorant in a typical propane gas may vary from about 5 ppm to about 20 ppm, more typically from about 7 ppm to about 15 ppm, and often about 8-12 ppm. K ratios and expected odorant levels for other thiol odorants in other hydrocarbon gases may be determined empirically or estimated based on the experience with ethanethiol in propane gas.

Fitness Characteristics of Odorant Meter for Field Use

To be most useful in the field, the odorant meter should be present on each service truck; the instrument should be easily carried, weigh no more than 5 to 10 lb, and run on battery power for at least a typical day's use. It should cost no more than about $1000 per unit, preferably less than $700, preferably less than $500. It should be housed in a durable but lightweight housing that may be constructed of metal or plastic resin.

Given the variability in sensitivity of the human nose to detect odorants, an accuracy of about 10% is deemed adequate. Of course, higher accuracies of 8%, 5%, 3% or more are preferred. Perhaps more importantly, the results of the meter should be objective and reproducible regardless of who is operating the instrument. In addition, the method used to determine odorant concentration must be resistant to errors caused by impurities in the propane. These impurities include heavy ends, lubricating oils, materials leached from transfer hoses, dirt, and moisture. See, e.g. *Liquefied Petroleum Gases*, A. F. Williams and W. L. Lom, 1982.

As noted above, propane odorants are generally added so that there is somewhat less than 10 ppm of odorant in the propane vapor. A useful detector device must therefore be sensitive at the sub-10 ppm level. In order to achieve a 10 percent accuracy level, the meter must be able to distinguish odorant levels of 1 ppm.

Quartz Crystal Microbalance-Based Sensors

There is a known group of crystalline substances that experience the piezoelectric effect. The piezoelectric effect has found applications in high power sources, sensors, actuators, frequency standards, motors, etc., and the relationship between applied voltage and mechanical deformation is well known. This feature allows probing an acoustic resonance by electrical means. Quartz is the most studied and most prevalent crystal that exhibits the piezoelectric effect ("piezo-crystal") and will be used for the ensuing exemplary description of a quartz crystal microbalance (QCM)—which is but one example of a piezo-crystalline substrate that is a sensitive and cost effective solution for detection of odorants in hydrocarbon gases. Other natural and synthetic materials that exhibit piezoelectric effect include Berlinite (AlPO4), a rare phosphate mineral that is structurally identical to quartz, sucrose (table sugar), Rochelle salt, Topaz, diamonds, and the Tourmaline-group minerals. Most piezo-crystals exhibit frequency drift as the temperature varies.

Various crystal cuts of quartz (and of other piezo-crystals) are known and described in the literature. See, e.g. *Crystals and Oscillators*, Jerry Lichter, JL9113 Rev C. an NEL Frequency and Controls Application Note published at: http://www.nelfc.com/app_notes.html (web accessed 4 Dec. 2013, original publication date unknown); and *Recent Advances in Quartz Crystal Microbalance-Based Sensors*, Sandeep. K. Vashist and Priya Vashist, Journal of Sensors, Vol. 2011, Article ID 571405, 2011. The classification of crystal cuts as AT, BT, SC, DT, CT, and GT has to do with the method by which the waves are propagated in the crystal. AT, BT, and SC cuts propagate by thickness shear mode vibration and are preferred. DT, CT, and GT cut crystals propagate by face shear mode vibration.

For AT cut crystals, the frequency constant is 1.661 MHz-mm, and is generally limited to approximately 40 MHz on the fundamental mode for small diameter blanks. Using contouring techniques the low end of the AT frequency range is approximately 500 kHz, but is dependent on holder size. The BT cut, having a frequency constant of 2.536 2.536 MHz-mm, can extend the upper frequency range above that of the AT cut to more than 50 MHz. The BT cut is not as widely accepted as the AT cut because of its poorer temperature characteristics in most applications; however, the use of a suitable reference sensor may obviate this problem. The frequency constant for the SC cut is 1.797 MHz-mm. However, this cut is also less preferred due to the complexities introduced by the non-orthogonal axes relative to the plane of propagation.

The resonant frequency of oscillation of the quartz crystal is partially dependent on the thickness and cut of the crystal. As mass is deposited on the surface of the crystal, the frequency of oscillation decreases from the initial value. This occurs whether the mechanism is a change in thickness or simply a mechanical dampening With some simplifying assumptions, this frequency change ($\Delta F$) can be quantified and correlated precisely to the mass change ($\Delta Ms$) using the Sauerbrey equation: $\Delta F/F = -\Delta Ms F/A\rho N$, where F refers to frequency (MHz), $\Delta Ms$ is the incremental mass of a substance coated on the crystal surface (g), A is the area coated ($cm^2$), $\rho$ is the density of the crystal, and N is the frequency constant. Using the density and frequency constant for AT-cut quartz crystals, and rearranging, the equation distills to: $\Delta F = -2.3 \times 10^6 (F^2)(\Delta Ms/A)$. See, e.g. *Applications of the Piezoelectric Crystal Detector in Analytical Chemistry*, J. Hlavay and G. G. Guilbault, Analytical Chemistry, Vol. 49, No. 13, November, 1977).

Figures 2A, 2B:
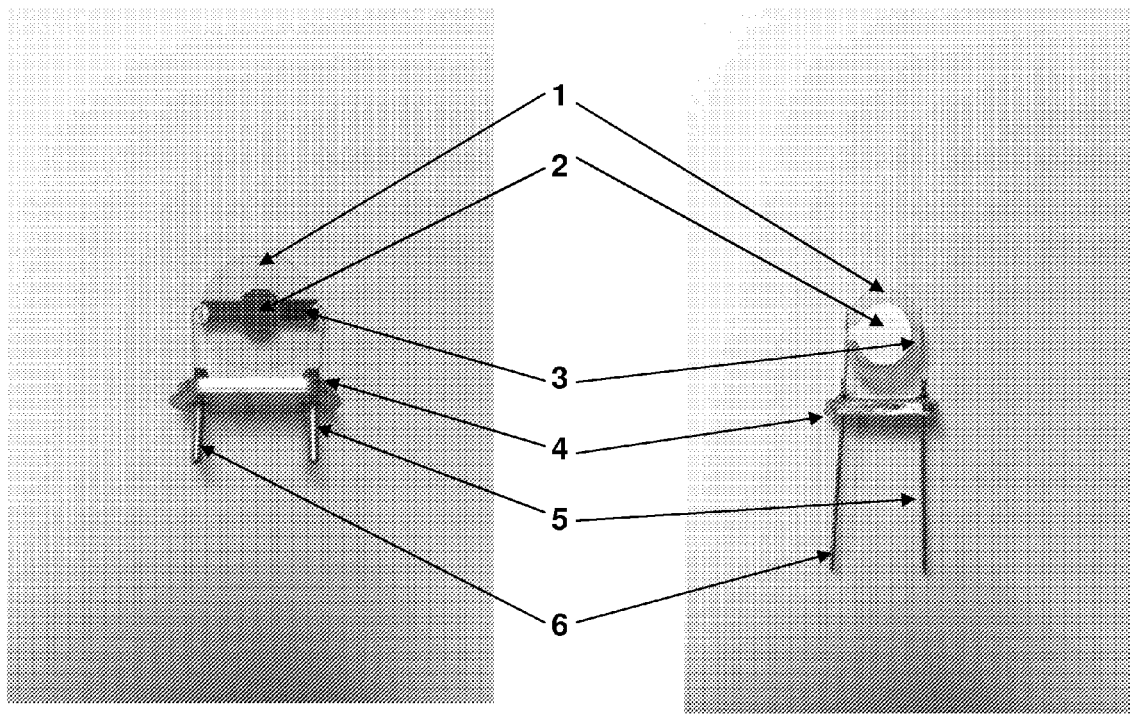
FIGS. 2A and 2B show representative QCM sensors.

FIGS. 2A and 2B illustrate two QCM-based sensors, also referred to herein as QCM sensors or simply "sensors." FIG. 2A illustrates a 10 MHz QCM and FIG. 2B illustrates a 2.4576 MHz QCM, like those used in the Examples. Each QCM has a quartz crystal substrate 1 mounted in a holder or bracket 4. Each QCM has two electrodes 2 and 3, sometimes referred to as inner and outer, or front and back, although the devices are symmetric and reversible. The electrodes 2, 3 are electrically connected to pins 5, 6 for ease in connecting the crystal electrically into circuitry, described later. QCM sensors exploit the gravimetric features of piezo-crystals, and in particular of AT cut quartz crystals, to measure very small changes in mass. The crystal is part of an oscillator circuit and the frequency of oscillation changes when the coating on the crystal is exposed to a material which reacts with the coating. Sensors based on the QCM principal use a quartz crystal that is coated with a reagent sensitive to the analyte of interest. QCM-based detectors have been made for many analytes, including ammonia, ozone, formaldehyde, toluene, water vapor, amines, nerve gases, a nerve gas stimulant, DMMP (Dimethyl Methylphosphonate), sulfur dioxide, and many others. Vashist and Vashist, have reviewed a number of QCM sensors described in the literature. See *Recent Advances in Quartz Crystal Microbalance-Based Sensors*, Sandeep. K. Vashist and Priya Vashist, Journal of Sensors, Vol. 2011, Article ID 571405, 2011.

Specific circuits capable of producing acceptable oscillation are well known in the art. A representative sampling are shown in FIG. 3, which is taken from section 5.19 of the well known text: "The Art of Electronics $2^{nd}$ Edition", by Paul Horowitz and Winfield Hill, Cambridge University Press, 1989. Some circuits have even acquired names like the Pierce oscillator (FIG. 3A) and the Colpitts oscillator (FIG. 3B). Many others are within the skill of those in these arts. AT cut quartz crystals oscillating at frequencies from about 1 to 40 MHz are suitable, or from about 2 to 20 MHz, with about 5-15 MHz being most common. A specific circuit variation, having parallel Colpitts oscillators, an analog multiplier, and a frequency-to-voltage converter is shown in FIG. 5 and discussed later.

FIGS. 4A to 4C show the frequency response curves and the detectable frequency shifts that occur in the presence of a particular analyte. FIG. 4A shows the frequency shifts when concentrations of toluene ranging from 200 to 1000 ppm were detected on various thicknesses of a coating of poly(3-hexylthiophene) (p3HT). The coating films were made to increasing thicknesses by means of applying 1 to 5 scans of cyclic voltammetry. This work is described in more detail in *Polymer coated quartz crystal microbalance sensors for detection of volatile organic compounds in gas mixtures*, Si, et al. Analytica Chimica Acta, 597 (2007) 223-230, from which FIG. 4A is a representation of their FIG. 1. FIG. 4B shows the frequency shifts when a nerve gas stimulant, DMMP (Dimethyl Methylphosphonate), was detected over a period of time on 10 MHz crystals coated with proprietary polymers. This work is described in more detail in "*Polymer-Coated Piezoelectric Quartz Crystal Sensor for Sensing the Nerve Agent Simulant Dimethyl Methylphosphonate Vapor,*" S. Maji, et al., J. Applied Polymer Science, February 2010, page 22, on which FIG. 4B is based. FIG. 4C shows the frequency shifts when sulfur dioxide ($S_{O2}$), was detected in the presence of water vapor (curve 2) and without water vapor (curve 3) on 9 MHz crystals. Curve (1) represents water vapor alone. This work is described in more detail in "*An Application of Artificial Neural Networks. Simultaneous Determination of the Concentration of Sulfur Dioxide and Relative Humidity with a Single Coated Piezoelectric Crystal,*" W. Hongmei, et al., Anal. Chem. 1997, 69, 699-702, from which FIG. 4C is a representation of their FIG. 3.

FIG. 4D shows the frequency shifts when methyl mercaptan (methanethiol, $CH_3SH$), was detected using a poly (ethylene imine) (PEI) film as a polymeric layer on top of a porous $Al_2O_3$ base used to increase the surface area. The PEI film was coated onto the base using the sol-gel method. The developed sensor detected 100 ppb of $CH_3SH$ gas but had interference with moisture, which the authors indicate may be corrected by using humidity sensor as feedback source. This work is described in more detail in M. Kikuchi and S. Shiratori, "*Quartz crystal microbalance (QCM) sensor for $CH_3SH$ gas by using polyelectrolyte-coated sol-gel film,*" Sensors and Actuators B, vol. 108, no. 1-2, pp 564-571, 2005, from which FIG. 4D is a representation of their FIG. 15. Other frequency response curves for detecting thiols are described in the examples.

Figure 1:
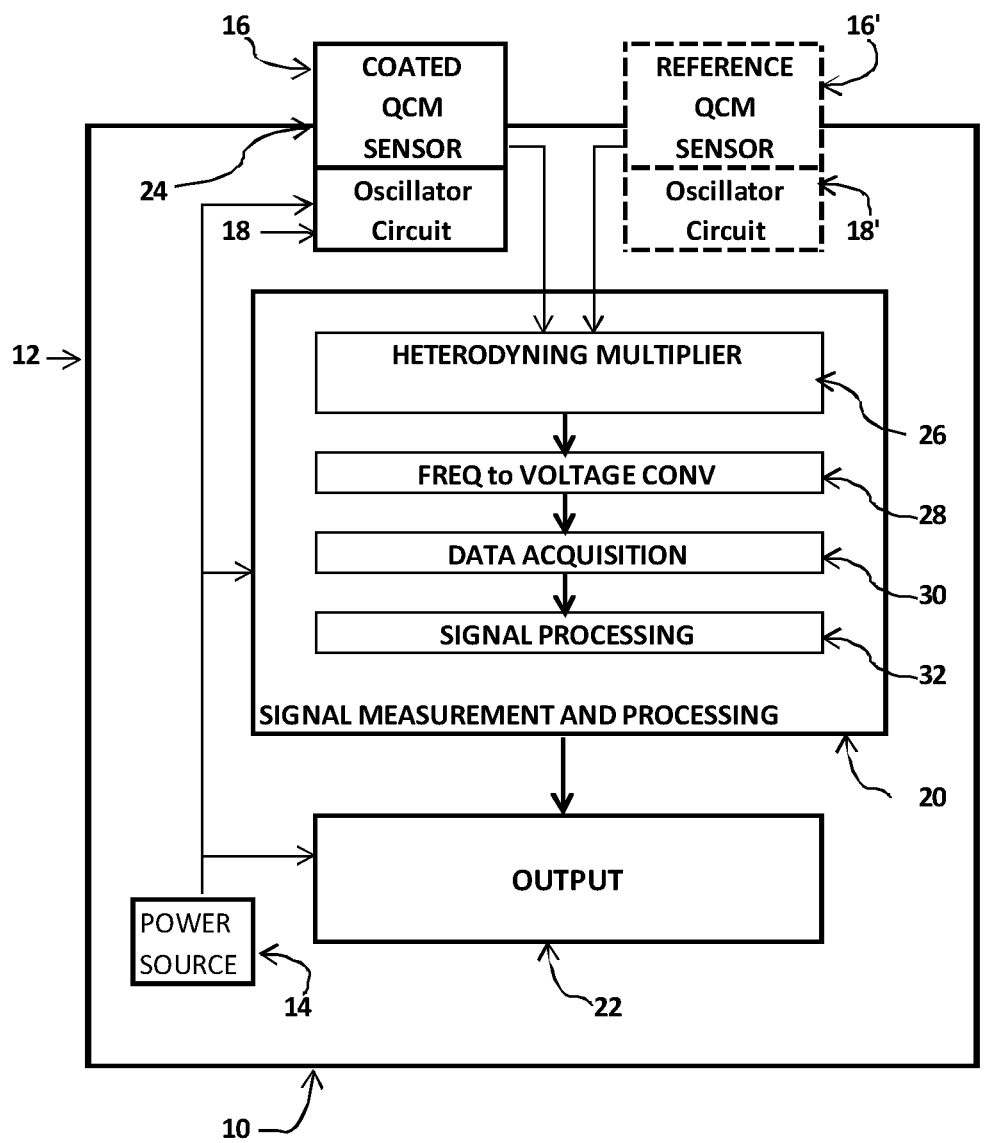
FIG. 1 is a schematic illustration of a detection device of the present invention, and shows an optional, alternate embodiment in dashed lines.

Referring now to FIG. 1, an embodiment of a portable detection device 10 in accordance with the invention is illustrated in block diagram form. The device 10 includes a housing 12 into which are secured: a power source 14; one or more QCM sensors 16, 16' and associated oscillator circuits 18, 18'; a signal processing module 20; and an output 22. The housing has at least one opening 24, into which a QCM sensor 16 is fitted. Depending on the specific coating chemistry (discussed later) in some embodiments, the sensor 16 may be permanently installed and reusable; but in other embodiments the chemistry is irreversible and the sensor 16 is for "single use." In these latter types of embodiments, it is desirable to make the sensor 16 a "plug-in" module with terminal pins or contacts that electrically connect to the circuitry inside. In a variation, a second QCM sensor 16' may be employed. Typically the second sensor 16' is a reference sensor, which will be described in more detail later.

A powered oscillator circuit 18 containing the QCM sensor 16, 16' receives current from the power source 14, causing the QCM to oscillate at a resonant frequency, setting up a standing shear wave in the crystal. In quartz AT cuts, the Q factor, which is the ratio of frequency and bandwidth, can be as high as $10^6$. Such a narrow resonance leads to highly stable oscillators and a high accuracy in the determination of the resonance frequency. Using a QCM sensor with these characteristics and properties provides great sensitivity and accuracy to the sensor of the device. Common equipment allows resolution down to 1 Hz or less on crystals with a fundamental resonant frequency in the 1-20 MHz range.

The standing wave frequency is detected by one of several possible frequency detection systems within the signal measurement and processing circuitry module 20, and a result is sent to the output 22. The output 22 is typically a visible display, such as an LED or LCD screen, or computer, but may alternatively or in addition include an audible or other detectable output. Power source 14 also supplies power for the signal measurement and processing module 20 and for the output 22 as needed. The power source may be any type of battery or current generator.

Note that when a second QCM sensor 16' is present, it will have its own oscillator circuit 18', the "prime" designation and dashed lines indicating an optional feature. Within the signal measurement and processing block 20, there are number of options. There may be one or more frequency counter circuits (not shown), or there may be a "beat frequency" or "heterodyning" circuit 26 that compares two frequencies directly and generates a third, differential frequency that may be counted more easily, more more quickly or more inexpensively. Such heterodyning circuits are well known in electronics as analog multipliers. Module MPY634 (Texas Instruments) is one example that produces a sum of two input frequencies and a difference between two input frequencies, one of which is typically filtered out. This frequency output ("delta-frequency") may be further manipulated and processed. Block 28 illustrates a frequency—to—voltage convertor, which is also a well known electronic component, such as module LM2907M (Texas Instruments).

The invention further contemplates that three or even more QCM sensors may be employed depending on design characteristics of the system. When more QCM sensors are employed, each will have its own oscillator circuit. If two or more QCM sensors are employed usually at least one is a reference or control sensor. Reference sensors may be configured in several ways: (1) they may contain no coating and thereby control for environmental variables such as temperature or humidity that can cause frequency drift in the QCM sensors; (2) they may contain a vehicle only coating, without a capture reagent, and thereby control for coating variability; (3) they may contain a vehicle coating including an inert salt, such as sodium chloride; or (4) they may contain a coating that responds specifically to a known potentially interfering substance, in each case resulting in improved specificity accuracy. In multiple sensor systems, any combination of types of controls may be employed, and an interference resolution module may become part of the signal processing module. Using suitable reference sensors ensures that many unwanted errors can be nulled out with the signal processing circuitry.

It is not necessary that the resonant frequency of a reference QCM exactly match that of the reagent coated sample QCM, although this may have some advantages. The signal-to-noise ratio and dynamic range of frequency changes may be easier to manage in the circuit if the frequencies of the two crystals are not too divergent. Thus, it may be advantageous to employ a reference crystal having a coating mass that closely matches the mass applied to sample crystal as the capture coating.

Frequency counters are also well known, albeit somewhat expensive, electronic components and need little description here. Synchronous, asynchronous, ring, flip-flop, shift registers, etc. are all examples of counting devices. Portability is important so smaller devices are preferred. An exemplary free-standing counter, the IBQ2006ST is commercially available, as are counters manufactured by Yaesu, of Japan. However, it is to be understood that, if a frequency counter is used, it would likely be included within the same housing 12. Although suitable frequency counters are available, they may also be disadvantaged for another reason. Because of the errors inherent in determining a small difference between two large numbers, if multiple frequency counters were used, the individual frequency counters would need to have a very high level of accuracy, which would add greatly to the cost.

In some embodiments, such as the one shown in FIG. 5, two quartz crystals are oscillated at their resonant frequency in a parallel Colpitts oscillator configuration. The Colpitts oscillators consists of a gain device connecting its output as the input in a feedback loop containing a parallel resonant circuit which functions as a bandpass filter setting the frequency of oscillation. Direct current voltage is supplied to the oscillators resulting in a radio frequency signal outputs.

The frequency outputs from the oscillators are sent to an analog multiplier (e.g. Module MPY634) configured such that the delta-frequency between the two crystals is returned. The heterodyned delta-frequency measurement is advantageous for a number of reasons. First, it eliminates or controls for the environmental effects of temperature, moisture, non-selective adsorption of other contaminants, etc. which would confound the reading if only a single crystal were used. These are "subtracted out" in the heterodyned format, as described above for a "beat frequency." Second, it eliminates the need for a second frequency counter, which can be an expensive component of the circuitry. Hence, it greatly relaxes the accuracy that would be required if two frequency counters were used. Additionally, if the frequency data is converted to analog data, such as voltage, the need for expensive frequency counters may be eliminated completely.

The output of the frequency to voltage converter is an analog voltage, and this is of course paired to the time points at which the frequency data was measured, and may be scaled or normalized. Typical circuitry components like resistors and capacitors may be employed to provide the scaling such that the analog voltages are within a detectable range while minimizing signal-to-noise ratio.

The analog voltage is sent to a data acquisition system (DAQ) 30 which converts it to a digital voltage. The DAQ records and compiles the data in a format that gives columns of time values and digital voltage values representing the delta-frequencies. From a look-up table or a mathematical manipulation (e.g. linear regression), the digital voltages may be converted to digital frequencies. This data may be represented graphically, as in FIGS. 6 and 7, or further manipulated by analog circuitry or signal processing to convert the output voltage to a more useful readout.

The odorant sensor device must be initially calibrated using at least two, and preferably three, accurately known concentrations of ethanethiol for testing the meter at low, medium, and full-scale readings; for example, 3 ppm, 25 ppm, 50 ppm respectively. After this initial calibration, sensors can be manufactured with substantially the same sensitivity.

Signal Processing

Digital data from the DAQ (30) may be manipulated mathematically in signal processing module (32) or computers. In one method or manipulation, the integrated area under the frequency-time curve provides an overall metric in terms of reacted thiol. Specifically, an increased odorant concentration results in a faster reaction, and therefore, a greater area under the frequency-time curve as measured in frequency-seconds. In some cases, the overall curve is normalized by the maximum frequency. The advantage of the normalization approach is that non-uniformity in crystal response can be eliminated and therefore the steepness in the ascending frequency curve dictates the magnitude of the area under the curve measured in seconds.

In another method of manipulation, the steepness of the ascent curve is directly calculated by calculating a numerical first derivative. Alternatively, the derivative is calculated by fitting the ascent curve to a function and then analytically differentiating the function providing a measurement in Hz/second (raw data) or inverse seconds (normalized data). In other methods, a second derivative might be calculated and/or exponential or moving averages may be examined. Many signal processing manipulations are possible, both on digital values and on the analog data prior to conversion to digital.

Lastly, depending on the reaction mechanism, the frequency-time curve may show non-monotonic behavior (as in FIG. 6). In such cases, a two-phase reaction proceeds first as an increase in mass, thus increasing the delta-frequency reading; followed by a reduction in delta-frequency, as a volatile product is formed and evaporates, thus reducing mass on the crystal. In such cases, the integral under the initial curve before concavity changes (marked by broad arrow in FIG. 6) can be used as a metric for gas phase thiol concentration. For higher gas phase concentrations of thiol, the initial reaction (formation of metal-thiol complex) is fast and a larger area under the initial curve is collected. FIG. 7 shows a calibration curve where the area underneath the initial curve (first few seconds only, see arrow) is calculated from normalized frequency. As evidenced by the Figure, the trendline curves are pronounced and with limited error. The resulting fitted curve can then be used as a reference to determine the amount of thiol present in a gas sample with an unknown odorant concentration.

QCM Coatings Criteria

Ideally the QCM sensor is not only sensitive, but also specific for the analyte of interest, meaning it does not react to any appreciable extent to the other components of the reaction mixture, including impurities. In particular, oleophilic polymer coatings should be avoided as they would be expected to react significantly with the hydrocarbons in the gas and therefore be less specific. Thus, many hydrocarbon polymers and films must be avoided. The coating for the odorant sensor must be a material that either exhibits a specific absorptive attraction for the odorant—which may or may not be reversible—or undergoes a chemical reaction with the odorant—which typically, but not necessarily, is irreversible. In either case, the accumulation of mass captured by the coating on the crystal detectably alters its oscillation frequency, and this can be correlated as shown by Sauerbrey.

In general, the coatings may be oleophobic. Merriam-Webster defines oleophobic as "having or relating to a lack of strong affinity for oils." While various other definitions have been proposed for oleophobicity, they generally all relate to the extent to which the compound tends to avoid oil-like hydrocarbons. As used herein, an "oleophobic" coating is one in which adherence or capture of hydrocarbons is negligible; meaning that the coating will capture or bind hydrocarbons in an amount not more than 6%—preferably less than 4%—of the amount of the thiol-odorant captured or bound by the same coating.

In some embodiments, the coating may require no specific capture reagent and may merely adsorb the thiol odorant, and the adsorption may be reversible or essentially irreversible under the reaction conditions. In other embodiments, the coating may include a specific reagent for capturing or binding the thiol odorant. As previously noted, the "capturing" may be reversible or irreversible, and may occur by any of several mechanisms, including but not limited to adsorption, chelation, coordination complexes, or bond formation, such as a covalent bond. Thus, a coating in some embodiments comprises a "capture" reagent and a vehicle for dispersing the capture reagent on the QCM piezo crystal substrate.

Another important fitness criteria for coatings is stability over time. To ensure stability, the coating should not change appreciably in mass. This means that the vehicle and capture reagent, once dried and calibrated, should not have a vapor pressure that would permit evaporative losses of either. Also, the coating should not be corrosive to the electrodes or other components with which it comes in contact, so acids and other corrosive vehicles should be avoided or else more expensive metals may be required for electrodes.

Reagents

A number of oleophobic reagents have been identified that are specific for thiol odorants in the hydrocarbon environment of natural gas. Some are reviewed by Knight and Verma in *Measurement of Odorant Levels in Natural Gas*, Arthur R. Knight and Arun Verma, Ind. Eng. Chem. Prod. Res. Dev. Vol. 15, No. 1, 1976, incorporated by reference. These include:

(a) Bis(p-nitrophenyldisulphide) in a phosphate buffer at pH 8 was shown to bind mercaptans, although the resulting color intensity effect was not found to be reliably concentration dependant.

(b) Mercury perchlorate with pyridine in an aqueous acetone solution caused formation of a white precipitate although no blue color as had been reported.

(c) Sodium nitrate and glacial acetic acid in aqueous solution reacted with mercaptans to produce a green color in solution, but bubbling of natural gas through the solution was found not to produce the color, probably due to insufficient contact time for the reaction to occur.

(d) Sodium nitroprusside in aqueous NaOH produced a green color in the presence of mercaptans, although the resulting color intensity effect was not found to be reliably concentration dependant. Similarly, $NH_4OH$ as the base produced a linearly correlated reddish color, but not when gas was bubbled through the solution.

(e) Phosphomolybdic acid in aqueous NaOH reacted with mercaptans to produce a blue product but the product appeared to be somewhat unstable.

(f) N-Ethylmaleimide in 2-propanol was found to react with mercaptans to produce a red-pink product and the color intensity effect varied linearly with concentration of mercaptan. This effect was maintained on bubbling of an odorant-containing gas stream through the solution, but the results were not reproducible in the presence of even trace quantities of water.

Many of the colorimetric chemistries described by Knight and Verma and summarized above would be unsuitable for colorimetric determination of thiol odorants in hydrocarbon gases—which easily would contain traces of moisture. However, applicant's use of these chemistries does not rely on a colorimetric effect. Therefore, applicant believes that they will function as suitable coating reagents for the QCM sensors. They need not produce color, they only need to add mass to the sensor in order to alter the oscillation frequency.

An alternative reagent coating system is described in M. Kikuchi and S, Shiratori, "*Quartz crystal microbalance (QCM) sensor for $CH_3SH$ gas by using polyelectrolyte-coated sol-gel film*," Sensors and Actuators B, vol. 108, no. 1-2, pp 564-571, 2005. They describe a QCM-based sensor for the detection of methyl mercaptan ((aka methanethiol, $CH_3SH$) in breath, as methanethiol can be a component of halitosis (bad breath). They use a poly(ethylene imine) (PEI) film as a polymeric layer, coated over a porous base ($Al_2O_3$) designed to increase the surface area of the capture reagent on the QCM. The developed sensor detected 100 ppb of $CH_3SH$ gas but had interference with moisture, a component of breath. The authors speculate that moisture interference may be corrected by using humidity sensor as feedback source.

Applicants have found that other reagents are quite suitable within the coating fitness criteria. For example, salts of certain cationic metals have been found to work well, designated generically as $M^+A^-$, where M is a positively charged metal ion and A is a counter anion. It should be understood that if either the metal or counter anion is di- or tri-valent, the comparable anion/metal is replicated sufficient times to balance the molecule to neutrality; for example $M^{+2}(A^{-1})_2$ or $(M^{+3})_2(A^{-2})_3$. Metals that form useful salts may be selected from groups 10 and 11 of the periodic table; for example salts of nickel, palladium, platinum, copper, silver, and gold are encompassed. In certain embodiments, transition metals from the fifth period are useful as metal salts, for example, salts of yttrium, zirconium, niobium, molybdenum, ruthenium, rhodium, palladium, silver, and cadmium.

The anions for salt formation may be essentially any anion, subject to solubility in the desired vehicle and other fitness criteria. Some anions of interest include, but are not limited to, nitrates, nitrites, acetates, sulfates, sulfites, chlorides, iodides, etc. In certain embodiments, the metal salt is a salt of a metal from groups 8 through 12. In other embodiments, the metal salt is a salt of a metal from group 10 or group 11. In some embodiments the salt is a silver salt, such as silver acetate, silver nitrate, or combinations thereof. In other embodiments, the metal salt is selected from copper salts, such as copper acetate, copper nitrate, or copper sulfate. In other embodiments, the metal salt is a salt of platinum or palladium, such as palladium chloride or palladium iodide, or palladium nitrate. In other embodiments, the metal salt is a salt of ruthenium or rhodium.

In some embodiments, depending on the specific reagents, the thiol-detecting reaction may be bi-phasic, and the delta-frequency vs. time curve may be non-monotonic (as in FIG. 6). For example, if ions or radicals remaining on the surface of the crystal that are not involved in the reagent-thiol complex can recombine to form volatile products, the process may initially show increased mass on the crystal, as thiol-odorant is captured, followed by decreased mass as the volatile product evaporates. This appears to be the case when certain acetates are used as a reagent. For example, silver acetate and ethanethiol can react to form silver-mercaptide (Reaction 1 below) while the ethane group of the ethanethiol compound interacts with acetate forming volatile ethyl acetate (Reaction 2 below). Similarly, methanethiol could form volatile methyl acetate.

Reaction 1:

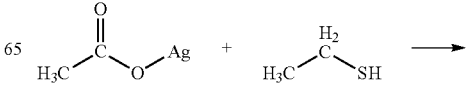

-continued

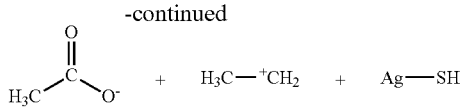

Reaction 2:

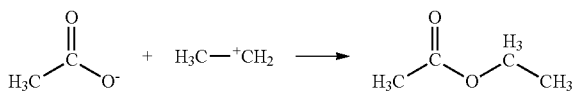

Vehicle Systems

The capture reagent must be coated onto the QCM for the sensor to operate to capture the thiol, and thereby gain the weight that dampens the oscillation frequency. A vehicle is one mechanism to accomplish this. Vehicles described herein may be solutions or suspensions or sol-gels. The coating (i.e. capture reagent plus vehicle) may be applied to the crystal using a variety of techniques, including direct application by painting, spraying, dipping, brushing, pipetting, swapping, and any other method which transfers the coating from a supply solution to the crystal surface, with or without the evaporation of a solvent. If the vehicle is a solution, it may contain the capture reagent dissolved, or within a colloidal suspension, in one or more solvents.

Water has been found to be a suitable solvent, as have various alcohols. Polar solvents may be desirable to enhance the oleophobic nature of the coating. Solvents may include, but are not limited to, water, methanol, ethanol, n-propanol, isopropanol, acetone, dilute acetic acid, and glycerol. Solvents may be applied and the solvent evaporated by drying or baking. However, the solvent should not have such a low vapor pressure that it evaporates before the capture reagent is dispersed uniformly.

If two solvents is used, there is generally a primary solvent and a co-solvent and the system is referred to as a binary vehicle. Similarly, if two-co-solvents are used, the vehicle system is "ternary" etc. The primary solvent may comprise from about 50 wt % to 99.99 wt % in a binary system and from about 34 wt % to 99.99 wt % in a ternary system. Co-solvents may be from 0.01 wt % to about 50 wt %, but often are from about 0.1 wt % to about 20 wt %. In binary and ternary systems, the co-solvent(s) may have surface tensions that are the same or different from that of the primary solvent. If different, the co-solvent may have a higher or lower surface energy. Generally speaking, low-surface-tension solvents and co-solvents aid in wetting the crystal to ensure a more uniform coating is applied. So if a primary solvent does not sufficiently wet the crystal to apply a uniform coating, one or more co-solvents having lower surface tension may be added. Another factors for choosing a solvent/co-solvent system include solubility of the reagents in the system. Thus, an acid or base may be used as a co-solvent to shift the pH slightly to improve solubility.

Optionally, the vehicles may include surfactants or dispersants to aid in distributing capture reagent uniformly on the crystal surface. Some example of dispersants include aliphatic phosphate esters (e.g. CHEMFAC PB-139), alkyl sulfates (e.g. sodium dodecyl sulfate (SDS) and ammonium lauryl sulfate), alkyl-ether sulfates (e.g. sodium laureth sulfate and sodium myreth sulfate), docusates (e.g. dioctyl sodium sulfosuccinate, perfluorooctanesulfonate, and perfluorobutanesulfonate), carboxylates (e.g. sodium lauroyl sarcosinate and sodium stearate), and carboxylate fluorosurfactants (e.g. perfluorononanoate, perfluorooctanoate).

Optionally, the vehicles may include binders to aid in sticking the capture reagent on the crystal surface. Some example of binders include polymerized alkoxysiloxane oligomers and sodium silicate. Optionally, the vehicles may include gel-forming polymers. These may aid in dispersing capture reagent uniformly and securing it to the crystal surface. Sol gel systems may involve a polymer and a catalyst in combination with the solvent. Some example of sol gel systems include a polyethoxysiloxane precursor along with dibutyltin diacetate as a catalyst in a propanol or propanol and water vehicle. In other cases, acid-catalyzed tetra alkyl orthosilicates in alcohols have been used to generate sol gels. The ethoxysiloxane sol gel is described in more detail by Lam, P. et al. "Surface-tension-confined microfluidics." Langmuir 18.3 (2002): 948-951.

Optionally, the vehicles may contain dyes or pigments, or the reagents themselves may produce a color in solution. Such colors may facilitate the coating process. The colors have been found to serve as a quality control to aid in discerning the uniformity of the coating on the crystal.

EXAMPLES

Example 1: Silver Nitrate as Reagent

Commercial quartz crystal oscillators are obtained from a variety of readily available sources with a baseline resonant frequency of 2.4576 MHz. These are coated by pipetting 5 µL of a solution of 0.5 wt % silver nitrate dissolved in a 50:50 water/propanol co-solvent. The density of the 50:50 water/propanol mixture is 905.1 kg/m$^3$ leading to a total mass of solution of around 4.5 milligrams and a reagent mass of approximately 22 nanograms added to the crystal surface. Colpitts or Pierce oscillators are used to resonate the crystals as shown in FIGS. 1 and 3. Coating and reagent mass can be varied to change the overall signal strength although there are maximum amounts of around 2 wt % reagent, above which the reagent mass begins interfering with the ability of the crystal to oscillate.

Example 2: Silver Acetate as Reagent

Commercial quartz crystal oscillators having a baseline resonant frequency of 2.4576 MHz are coated with about 5 µL of a solution of 0.5 wt % silver acetate dissolved in 50:50 propanol and water co-solvent. The resulting mass added to the crystal is assumed to be similar to that in Example 1, adjusted for different weights of the anions. A coated sensor and an uncoated sensor are connected in a dual Colpitts oscillator circuit as shown in FIG. 5, including the analog multiplier and frequency-to-voltage convertor.

The coated sensors were exposed to various concentrations of odorant in propane: 0 ppm, 24 ppm, and 60 ppm. An uncoated sensor is used as a control. Results are shown in FIG. 6, where the various concentrations are easily differentiable, showing an excellent dose response. The biphasic reaction that exhibits non-monotonicity is discussed elsewhere herein. FIG. 7 shows that from the first few seconds of the reaction. The data exhibits low variability about the means, and linear ($R^2$=0.9795) and ($R^2$=0.9795) and polynomial ($R^2$=1.0 by definition for three points) regression calibration curves are fitted to the data.

Example 3: Silver Salt as Reagent in a Sol Gel

Commercial quartz crystal oscillators having a baseline resonant frequency of 2.4576 MHz are coated with 0.5 wt % silver nitrate in a sol gel. A poly(ethoxysiloxane) and propanol sol gel was generated using the technique outlined by Lam, P. et al. "Surface-tension-confined microfluidics." Langmuir 18.3 (2002): 948-951. The sol gel employed a polyethoxysiloxane precursor (9% w/w/) along with dibutyltin diacetate as a catalyst added at a ratio of 2 microliters per gram of precursor/solvent solution. Water was added (5% w/w) as co-solvent, reducing the % of low surface tension propanol to 86% with 9% ethoxysiloxane precursor and catalyst. This co-solvent system preserves ethoxysiloxane miscibility with the propanol, enhances reagent solubility in the co-solvent mixture, and maintains the same degree of wettability as in the original mixture. The density of this vehicle system is unknown, but it is assumed that the mass of reagent added to the crystal is in the range of a few to tens of nanograms. At time=0, the sensor was exposed propane containing 24 ppm ethanethiol odorant. Results using these sol gel sensors to detect the thiol compound are shown in FIG. 8. The quick increase in delta-frequency between the reagent coated and uncoated crystals indicates the mass increase in the thiol-selective crystal.

Example 4: Palladium Nitrate as Reagent

Commercial quartz crystal oscillators having a baseline resonant frequency of 2.4576 MHz are coated with about 5 µL of a 0.5 wt % solution of palladium nitrate ($Pd(NO_3)_2$) dissolved in an equal mass ratio of propanol and water. As in Example 1 (the weights of silver and palladium being close) the mass of coating and reagent added to the crystal are about 4.5 mg and 22 nanograms, respectively. A reference crystal was prepared with 0.5 wt % NaCl dissolved in an equal mass ratio of propanol and water thereby achieving approximately the same mass loading both test and reference sensors, so that the starting delta-mass should be roughly the same for the reagent and reference crystals, resulting in a delta frequency of near zero. The two sensors are connected in a dual Colpitts oscillator circuit as shown in FIG. 5, including the analog multiplier and frequency-to-voltage convertor. FIG. 9 (curve A) shows a response of around 5-7 Hz when exposed to 24 ppm ethanethiol in propane. This response can be enhanced by using crystals with higher resonant frequencies. Moreover, since palladium is responsible for complexing with the thiol, the anionic species can likely be interchanged to other compounds such as chloride or acetate so long as care is taken to preserve solubility within the delivery vehicle. $Pd(NO_3)_2$ has a strong color that aids in visually observing uniformity of distribution which is advantageous for quality assurance.

Example 5: Palladium Chloride as Reagent

Example 4 is repeated, but coating with 0.5 wt % palladium chloride as the thiol-selective reagent dissolved a blend of water and hydrochloric acid.

Example 6: Ruthenium Trichloride as Reagent

Commercial quartz crystal oscillators having a baseline resonant frequency of 2.4576 MHz are obtained and coated with 5 µL of a 0.5 wt % solution of ruthenium trichloride in a 50:50 propanol and water co-solvent, resulting in about 22 nanograms of reagent on the sensor. A coated sensor and an uncoated sensor are connected in a dual Colpitts oscillator circuit as shown in FIG. 5, including the analog multiplier and frequency-to-voltage convertor. FIG. 9 (Curve B) shows a response of around 3 Hz when exposed to 24 ppm ethanethiol in propane. This response can be enhanced by using crystals with increased resonant frequencies. Ruthenium complexes with the thiol in this reaction. Therefore, the anion is immaterial in this example and can be interchanged with other species so long as solubility is maintained.

It is reiterated that all references cited herein, including books, journal articles, published U.S. or foreign patent applications, issued U.S. or foreign patents, and any other references, are each incorporated by reference in their entireties, including all data, tables, figures, and text presented in the cited references.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

What is claimed is:

1. A portable device for detecting thiol odorants in a hydrocarbon gas, the device comprising a housing enclosing the following elements:
   i) a power source for producing a current;
   ii) a thiol sensor comprising
      a piezo-crystalline substrate disposed in the housing and located for gaseous communication with the hydrocarbon gas,
      a coating on the piezo-crystalline substrate, the coating capable of reacting specifically with and capturing thiol components from a gaseous phase thereby adding mass to the thiol sensor, while substantially not reacting with the hydrocarbon gas itself; and,
   iii) an oscillator circuit, the thiol sensor forming a part of the oscillator circuit,
      whereby, when powered by the power source, the piezo-crystalline substrate oscillates at a first frequency prior being exposed to thiol odorants in a gas, and at a second frequency after being exposed to thiol odorants in the gas and capturing thiols in the coating, the second frequency differing from the first frequency in proportion to the amount of thiol captured.

2. The invention of claim 1 wherein the piezo-crystalline substrate is a quartz crystal having a resonant frequency from about 2 MHz to about 20 MHz.

3. The invention of claim 1 wherein the coating comprises a metal salt reagent dispersed in an oleophobic solvent.

4. The invention of claim 3 wherein the metal salt comprises a metal from groups 10 or 11, or a transition metal from period 5.

5. The invention of claim 3 wherein the metal salt is a silver salt.

6. A portable device for detecting thiol odorants in a hydrocarbon gas, the device comprising a housing enclosing the following elements:
   i) a power source for producing a current,
   ii) a reference sensor comprising a first piezo-crystalline substrate disposed in the housing and located for fluid communication with the hydrocarbon gas; the reference sensor forming part of a first oscillator circuit capable of producing a reference oscillation frequency in response to a current input;

iii) a thiol sensor comprising a second piezo-crystalline substrate disposed in the housing and located for fluid communication with the hydrocarbon gas; the second piezo-crystalline substrate having a coating thereon, the coating capable of reacting specifically with and capturing thiol components from a gaseous phase thereby adding mass to the thiol sensor, while substantially not reacting with the hydrocarbon gas itself; the thiol sensor forming part of a second oscillator circuit capable of producing a second oscillation frequency in response to a current input; and, iv) circuitry for heterodyning the first and second frequencies to produce a third frequency representative of the amount of mass added to the thiol sensor as a result of thiol capture.

7. The invention of claim 6 wherein each of the first and second piezo-crystalline substrates is a quartz crystal having a resonant frequency from about 2 MHz to about 20 MHz.

8. The invention of claim 6, wherein the circuitry for heterodyning the first and second frequencies comprises an analog multiplier.

9. The invention of claim 6 wherein the coating comprises a metal salt reagent dispersed in an oleophobic solvent.

10. The invention of claim 9 wherein the metal salt comprises a metal from groups 10 or 11, or a transition metal from period 5.

11. The invention of claim 9 wherein the metal salt is a silver salt.

12. The invention of claim 9 wherein the metal salt is a metal acetate or a metal nitrate.

13. The invention of claim 12 wherein the thiol odorant is ethanethiol.

14. The invention of claim 9, wherein the reference piezo-crystalline substrate is uncoated.

15. The invention of claim 9, wherein the reference piezo-crystalline substrate is coated with the oleophobic solvent not containing the metal salt reagent.

16. A method for detecting thiol odorants in a hydrocarbon gas using the portable detector of claim 6, the method comprising:

outputting the oscillation frequency data of the sensors as they are exposed to a gas suspected to contain a thiol odorant for a time sufficient to allow the coating to capture thiols if present in the gas;

heterodyning the frequency data to produce a delta frequency data;

converting the delta frequency data to voltage data;

collecting the voltage data in a data acquisition module.

17. The invention of claim 16, further comprising performing one or more signal processing steps on the voltage data.

18. The invention of claim 16, further comprising converting the voltage data back to thiol concentration based on a standard calibration curve.

19. The invention of claim 18, further comprising performing one or more signal processing steps on the frequency data.

20. The invention of claim 16 wherein the hydrocarbon gas is propane or natural gas.

* * * * *